(12) United States Patent
Vanover et al.

(10) Patent No.: US 12,325,726 B2
(45) Date of Patent: Jun. 10, 2025

(54) ORGANIC COMPOUNDS

(71) Applicant: INTRA-CELLULAR THERAPIES, INC., New York, NY (US)

(72) Inventors: Kimberly Vanover, New York, NY (US); Peng Li, New Milford, NJ (US); Robert Davis, San Diego, CA (US); Yupu Qiao, New York, NY (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 911 days.

(21) Appl. No.: 17/415,667

(22) PCT Filed: Dec. 17, 2019

(86) PCT No.: PCT/US2019/066923
§ 371 (c)(1),
(2) Date: Jun. 17, 2021

(87) PCT Pub. No.: WO2020/131918
PCT Pub. Date: Jun. 25, 2020

(65) Prior Publication Data
US 2022/0073558 A1    Mar. 10, 2022

Related U.S. Application Data

(60) Provisional application No. 62/780,703, filed on Dec. 17, 2018.

(51) Int. Cl.
| | | |
|---|---|---|
| C07B 59/00 | (2006.01) | |
| A61K 31/58 | (2006.01) | |
| A61P 23/00 | (2006.01) | |
| A61P 25/00 | (2006.01) | |
| A61P 25/20 | (2006.01) | |
| C07J 43/00 | (2006.01) | |

(52) U.S. Cl.
CPC ......... *C07J 43/003* (2013.01); *C07B 2200/05* (2013.01)

(58) Field of Classification Search
CPC ..... C07J 43/003; C07J 43/00; C07B 2200/05; C07B 59/00; C07B 59/07; A61P 23/00; A61P 25/20; A61P 25/00; A61K 31/58
See application file for complete search history.

(56) References Cited

U.S. PATENT DOCUMENTS

| | | | |
|---|---|---|---|
| 5,232,917 A | 8/1993 | Bolger et al. | |
| 5,846,514 A | 12/1998 | Foster et al. | |
| 5,939,545 A | 8/1999 | Upasani et al. | |
| 6,277,838 B1 | 8/2001 | Upasani et al. | |
| 10,329,320 B2 | 6/2019 | Robichaud et al. | |
| 10,544,185 B2 | 1/2020 | Lv et al. | |
| 10,870,677 B2 | 12/2020 | Martinez Botella et al. | |
| 2004/0034002 A1 | 2/2004 | Hogenkamp | |
| 2006/0074059 A1 | 4/2006 | Goliber et al. | |
| 2009/0118248 A1 | 5/2009 | Chang et al. | |
| 2009/0131383 A1 | 5/2009 | Woodward | |
| 2016/0108080 A1 | 4/2016 | Botella et al. | |
| 2017/0240589 A1 | 8/2017 | Martinez Botella et al. | |
| 2020/0291059 A1 | 9/2020 | Salituro et al. | |
| 2022/0073558 A1 | 3/2022 | Vanover et al. | |
| 2022/0098231 A1 | 3/2022 | Fransesco et al. | |
| 2023/0416300 A1 | 12/2023 | Li et al. | |

FOREIGN PATENT DOCUMENTS

WO    WO 9521617    8/1995

OTHER PUBLICATIONS

Blake, et al., "Studies with Deuterated Drugs" Journal of Pharmaceutical Sciences, 1975, vol. 64, pp. 367-391.
Buteau, "Deuterated Drugs: Unexpectedly Nonobvious?" 10 J. High Tech. Law 22 (2009).
Sanderson, "Big interest in heavy drugs," Nature, 2009, vol. 458, pp. 269.
Hogenkamp, et al., "Synthesis and in Vitro Activity of 3β-Substituted-3α-hydroxypregnan-20-ones: Allosteric Modulators of GABA$_A$ Receptor," J. Med. Chem. 40:61-72 (1997).
Martinez Botella, et al., "Neuroactive Steroids 1. Positive Allosteric Modulators of the (GABA)$_A$ Receptor: Structure-Activity Relationships of Heterocyclic Substitution at C-21," J. Med. Chem. 58:3500-3511 (2015).
Martinez Botella, et al., "Neuroactive Steroids 2. 3α-Hydroxy-3β-methyl-21-(3-cyano-1H-pyrazol-1'-yl)-19-nor-5β-pregnan-20-one (SAGE-217): A Clinical Next Generation Neuroactive Steroid Positive Allosteric Modulator of the (GABA)$_A$ Receptor," J. Med. Chem. 60:7810-7819 (2017).
Wong, et al., "Synthesis of 3α-Hydroxy-21-(1'-imidazolyl)-3β-methoxyl-methyl-5α-pregnan-20-one via lithium imidazole with 17α-acetylbromopregnanone," Steroids 71:77-82 (2006).
Vanover, et al., "Response-Rate Suppression in Operant Paradigm as Predictor of Soporific Potency in Rats and Identification of Three Novel Sedative-Hypnotic Neurosteroids," J. Pharm & Exp. Therap. 291:1317-1323 (1999).
Vanover, et al., "Characterization of the Anxiolytic Properties of a Novel Neuroactive Steroid, Co 2-6749 (GMA-839; WAY-141839; 3α, 21-Dihydroxy-3β-trifluoromethyl-19-nor-5β-pregnan-20-one," J. Pharm & Exp. Therap. 295:337-345 (2000).

*Primary Examiner* — Sun Jae Yoo
(74) *Attorney, Agent, or Firm* — Hoxie & Associates LLC

(57) ABSTRACT

The invention relates to particular prodrugs and analogs of (3α,5α)-3-hydroxy-21-(1H-imidazol-1-yl)-3-methoxymethyl)-pregnan-20-one, in free or pharmaceutically acceptable salt and/or substantially pure form as described herein, pharmaceutical compositions thereof, and methods of use as sedatives, hypnotics, anxiolytics, and/or anesthetics, and methods for treatment of depression, anxiety, insomnia, epilepsy, and other central nervous system disorders, as well as to combinations with other agents.

28 Claims, No Drawings

ORGANIC COMPOUNDS

CROSS-REFERENCE TO RELATED APPLICATIONS

This application is a U.S. National Stage application under 35 U.S.C. § 371 of International Application No. PCT/US2019/066923, filed on Dec. 17, 2019, which claims priority to and the benefit of U.S. Provisional Application No. 62/780,703, filed on Dec. 17, 2018, the contents of each of which are hereby incorporated by reference in their entireties.

FIELD OF THE INVENTION

The invention relates to particular prodrugs and analogs of (3α,5α)-3-hydroxy-21-(1H-imidazol-1-yl)-3-methoxymethyl)-pregnan-20-one, in free or pharmaceutically acceptable salt and/or substantially pure form as described herein, pharmaceutical compositions thereof, and methods of use as sedatives, hypnotics, anxiolytics, and/or anesthetics, and methods for treatment of depression, anxiety, insomnia, epilepsy, and other central nervous system disorders, as well as to combinations with other agents.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes.

The neurotransmitter gamma-aminobutyric acid (GABA) has a profound influence on overall brain excitability because up to 40% of the neurons in the brain utilize GABA as a neurotransmitter. GABA interacts with the GABA receptor complex (GRC) to mediate its effects on the nerve cells throughout the nervous system, including the brain. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs, i.e., reduced neuron excitability. In other words, the higher the chloride ion concentration in the neuron, the lower the brain excitability and level of arousal.

The GRC plays a key role in the mediation of anxiety, seizure activity, depression and sedation. As a result, GABA and drugs that act like GABA to facilitate the effects of GABA (e.g., the therapeutically useful barbiturates and benzodiazepines (BZs), such as Valium®) produce their therapeutically useful effects by interacting with specific regulatory sites on the GRC. Accumulated evidence has now indicated that in addition to the benzodiazepine and barbiturate binding site, the GRC contains a distinct site for neuroactive steroids.

Neuroactive steroids occur endogenously. The most potent endogenous neuroactive steroids are 3α-hydroxy-5-reduced pregnan-20-one and 3α,21-dihydroxy-5-reduced pregnan-20-one, metabolites of hormonal steroids progesterone and deoxycorticosterone, respectively. As discussed in US 2017/0240589, incorporated herein by reference in its entirety, several recent clinical observations imply a crucial role for progesterone and deoxycorticosterone and their metabolites in the homeostatic regulation of brain excitability. This is manifested, for example, as an increase in seizure activity or symptoms associated with catamenial epilepsy, PMS, and PND, and a correlation between reduced levels of progesterone and the symptoms associated with PMS, PND, and catamenial epilepsy. However, progesterone is not consistently effective in the treatment of the aforementioned syndromes. Natural neuroactive metabolites of progesterone include pregnanolone and allopregnanolone and these metabolites may mediate at least some of the effects of progesterone and deoxycorticosterone.

The naturally occurring neuroactive steroids are generally unsuitable as pharmacological agents because they have short half-lives and have poor oral bioavailability, presumably due to rapid metabolism. One such steroid is allopregnanolone,

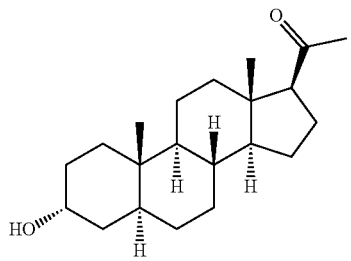

It is an endogenous neuroactive steroid showing promising pharmacologically activity, but it suffers from low oral bioavailability and a short half-life. Nevertheless, allopregnanolone is being pursued for intravenous treatment of epilepsy, depression and other CNS disorders.

New and improved neuroactive steroids are needed that act as modulating agents for brain excitability, such as sedatives, hypnotics and anxiolytics, as well as agents for the prevention and treatment of CNS-related diseases.

Synthetic and semi-synthetic neuroactive steroids are known in the art and have been studied as potential CNS drugs.

The addition of 3β-substitution has been shown to result in neuroactive steroids with potent oral activity but undesirably long half-lives. For example, sedative/hypnotic agents should preferably have an elimination half-life in humans of less than 5 hours to avoid residual next-day effects and accumulation on continued nightly dosing. It was previously discovered that 3β-methoxymethyl-substituted steroids maintain the desirable oral activity of other 3β-substituted neuroactive steroids, but with a duration action that made them useful as sedative/hypnotics and anesthetics. Such compounds are disclosed in, for example, U.S. Pat. Nos. 5,939,545 and 6,277,838.

3α-Hydroxy-3β-methoxymethyl-21-(1H-imidazol-1-yl)-5α-pregnan-20-one is a synthetic neuroactive steroid. Its primary molecular target is the γ-aminobutyric acid type A (GABA$_A$) receptor, where it acts as a positive allosteric modulator of GRC channel function. Like other classes of GABA$_A$ modulators, such as benzodiazepines and other benzodiazepine site ligands, neuroactive steroids have a number of potential indications, such as for the treatment of sleep disorders, anxiety, depression, and epilepsy. This compound has been disclosed in, for example, U.S. Publications 2004/0034002 and 2009/0131383, the contents of which are incorporated by reference in their entireties.

Clinical studies suggest that 3α-Hydroxy-3β-methoxymethyl-21-(1H-imidazol-1-yl)-5α-pregnan-20-one has the following pharmacokinetic properties in humans following oral dosing: (1) rapid absorption with Tmax ranging from about 1 to about 3 hours; (2) variable Cmax levels between subjects; (3) greater than dose-proportional Cmax values; and (4) T1/2 values that averaged approximately 12 hours across five different dosing groups. See Table 1, below. Pharmacokinetic parameters such as AUC, Cmax and tmax refer to mean values. The values reported in brackets correspond to standard deviations.

TABLE I

| Oral Dose (Fasted) | N | Tmax (h) | Cmax (ng/mL) | AUC (0-24) (ng/ml*h) | T1/2 (h) | AUC (0-last) (ng/ml*h) |
|---|---|---|---|---|---|---|
| 1 mg | 4 | 3.1 (1.7) | 1.3 (0.3) | 16.9 (2.8) | 13.8 (0.5) | 22.4 (3.2) |
| 3 mg | 4 | 2.8 (1.0) | 5.7 (1.7) | 54.6 (23.5) | 8.8 (2.7) | 65.6 (34.7) |
| 10 mg | 8 | 1.7 (0.6) | 26.5 (10.2) | 213 (87.0) | 13.1 (3.2) | 254 (115) |
| 30 mg | 4 | 2.1 (1.3) | 120 (27.8) | 952 (142) | 13.1 (1.0) | 1117 (185) |
| 60 mg | 4 | 1.8 (0.9) | 330 (109) | 2330 (767) | 12.5 (0.69) | 2608 (943) |

It would be advantageous, however, to develop derivatives of 3α-Hydroxy-3β-methoxymethyl-21-(1H-imidazol-1-yl)-5α-pregnan-20-one having improved pharmacokinetic properties, such as higher resistance to metabolic degradation or improved distribution and/or bioavailability.

SUMMARY OF THE INVENTION

The compound of Formula A, having the chemical name 2-(1H-imidazol-1-yl)-1-((3S,5S,8R,9S,10S,13S,14S,17S)-3-(methoxymethyl)-10,13-dimethylhexadecahydro-1H-cyclopenta[a]phenanthren-17-yl)ethan-1-one, and the common name 3α-Hydroxy-3β-methoxymethyl-21-(1H-imidazol-1-yl)-5α-pregnan-20-one, shown below is a potent positive allosteric modulator of the $GABA_A$ receptor. This compound my also interact with acetylcholine receptors and $5$-$HT_3$ serotonin receptors.

Formula A

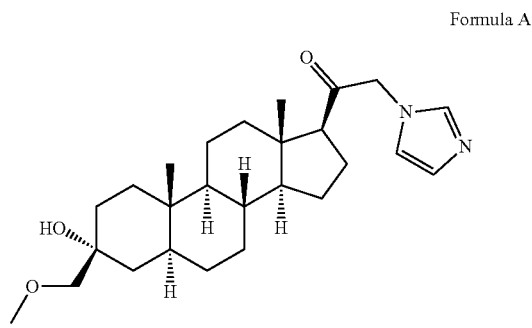

The Compound of Formula A is useful as a sedative/hypnotic or anesthetic, and for the treatment or prophylaxis of central nervous systems disorders, but there is a need in the art for analogs, such as isotopic analogs and prodrugs, of the Compound of Formula A that when administered to a patient can provide for improved therapeutic concentrations or improved pharmacokinetic distribution or dynamics. The present disclosure fills this need by providing Compounds of Formula I et seq., which are deuterated analogs and/or prodrugs of the Compound of Formula A. Due to their useful metabolic and pharmacokinetic profile, the Compounds of the present disclosure may be particularly suited for formulation as long-acting or extended-release compositions that when administered to a patient can provide for improved therapeutic amounts concentrations of the compound A and its analogs over an extended period of time.

In a first aspect, the present disclosure provides a compound (Compound 1) of Formula I:

Formula I

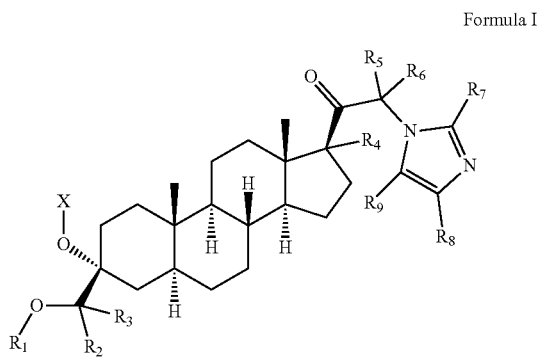

wherein:

X is selected from H, —(C=O)—$R_a$, —CH$_2$—(C=O)—O—$R_a$, and —CH$_2$—(C=O)—N($R_a$)($R_b$);

$R^1$ is selected from $CH_3$, $CDH_2$, $CD_2H$ and $CD_3$;

each of $R^2$ to $R^9$ is independently selected from H and D;

$R_a$ and $R_b$ are independently selected from H, $C_{1-20}$alkyl (e.g., methyl), and $C_{1-4}$alkyl-aryl (e.g., benzyl), in free or salt form (e.g., pharmaceutically acceptable salt form), for example in an isolated or purified free or salt form, provided that if $R^1$ is $CH_3$ and $R^2$ to $R^9$ are all H, then X is selected from —(C=O)—$R_a$, —CH$_2$—(C=O)—O—$R_a$, and —CH$_2$—(C=O)—N($R_a$)($R_b$).

In a second aspect, the present disclosure provides pharmaceutical compositions comprising the compounds of Formula I et seq., in combination with a pharmaceutically acceptable diluent or carrier.

In a third aspect, the present disclosure provides methods for the treatment or prophylaxis of central nervous system disorders amenable to amelioration using a $GABA_A$ receptor modulator (e.g., a positive allosteric modulator of the $GABA_A$ receptor), wherein the methods comprise the administration to a patient in need thereof a compound of Formula I or a pharmaceutical composition thereof.

In a fourth aspect, the present disclosure provides methods of inducing sedation or anesthesia in a patient in need thereof, wherein the methods comprise the administration of a compound of Formula I or a pharmaceutical composition thereof.

DETAILED DESCRIPTION OF THE INVENTION

In a first aspect, the present disclosure provides a compound (Compound 1) of Formula I:

Formula I

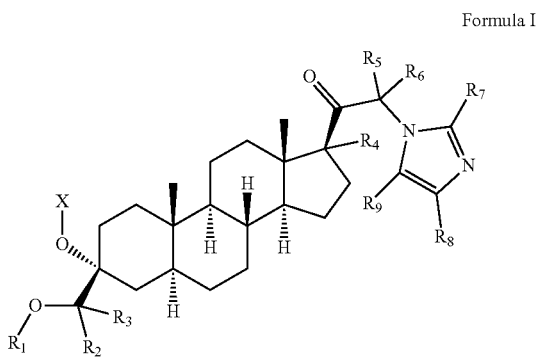

wherein:
X is selected from H, —(C═O)—$R_a$, —$CH_2$—(C═O)—O—$R_a$, and —$CH_2$—(C═O)—N($R_a$)($R_b$);
$R^1$ is selected from $CH_3$, $CDH_2$, $CD_2H$ and $CD_3$;
each of $R^2$ to $R^9$ is independently selected from H and D;
$R_a$ and $R_b$ are independently selected from H, $C_{1-20}$alkyl (e.g., methyl), and $C_{1-4}$alkyl-aryl (e.g., benzyl),
in free or salt form (e.g., pharmaceutically acceptable salt form), for example in an isolated or purified free or salt form,
provided that if $R^1$ is $CH_3$ and $R^2$ to $R^9$ are all H, then X is selected from —(C═O)—$R_a$, —$CH_2$—(C═O)—O—$R_a$, and —$CH_2$—(C═O)—N($R_a$)($R_b$).

The present disclosure provides additional exemplary embodiments of the Compound of Formula I, in free or salt form, for example in an isolated or purified free or salt form, including:

1.1 Compound I, wherein X is H;
1.2 Compound I, wherein X is selected from —(C═O)—$R_a$, —$CH_2$—(C═O)—O—$R_a$, and —$CH_2$—(C═O)—N($R_a$)($R_b$);
1.3 Compound I, wherein X is —(C═O)—$R_a$;
1.4 Compound I, wherein X is —$CH_2$—(C═O)—O—$R_a$;
1.5 Compound I, wherein X is $CH_2$—(C═O)—N($R_a$)($R_b$);
1.6 Compound I, or any of 1.1-1.5, wherein $R_a$ is H;
1.7 Compound I, or any of 1.1-1.5, wherein $R_a$ is $C_{1-20}$alkyl (e.g., methyl) or $C_{1-4}$alkyl-aryl (e.g., benzyl);
1.8 Compound I, or any of 1.1-1.5, wherein $R_a$ is $C_{1-20}$alkyl (e.g., methyl);
1.9 Compound I, or any of 1.1-1.5, wherein $R_a$ is $C_{1-4}$alkyl-aryl (e.g., benzyl);
1.10 Compound I, or any of 1.1-1.5, wherein $R_a$ is methyl;
1.11 Compound I, or any of 1.1-1.5, wherein $R_a$ is benzyl;
1.12 Compound I, or any of 1.1-1.11, wherein X is $CH_2$—(C═O)—N($R_a$)($R_b$) and $R_b$ is H;
1.13 Compound I, or any of 1.1-1.12, wherein $R^1$ is $CH_3$;
1.14 Compound I, or any of 1.1-1.12, wherein $R^1$ is $CDH_2$, $CD_2H$, or $CD_3$;
1.15 Compound I, or any of 1.1-1.12, wherein $R^1$ is $CD_3$;
1.16 Any of Compounds 1.1-1.15, wherein all of $R^2$ to $R^9$ are H;
1.17 Any of Compounds 1.1-1.15, wherein any one of $R^2$ to $R^9$ is D;
1.18 Any of Compounds 1.1-1.15, wherein any two of $R^2$ to $R^9$ are D;
1.19 Any of Compounds 1.1-1.15, wherein any three of $R^2$ to $R^9$ are D;
1.20 Any of Compounds 1.1-1.15, wherein any four of $R^2$ to $R^9$ are D;
1.21 Any of Compounds 1.1-1.20, wherein $R^2$ and $R^3$ are D;
1.22 Any of Compounds 1.1-1.21, wherein $R^5$ to $R^6$ are D;
1.23 Any of Compounds 1.1-1.22, wherein any one, two or three of $R^7$ to $R^9$ are D;
1.24 Compound I, or any of 1.1-1.23, wherein the compound is selected from the group consisting of:

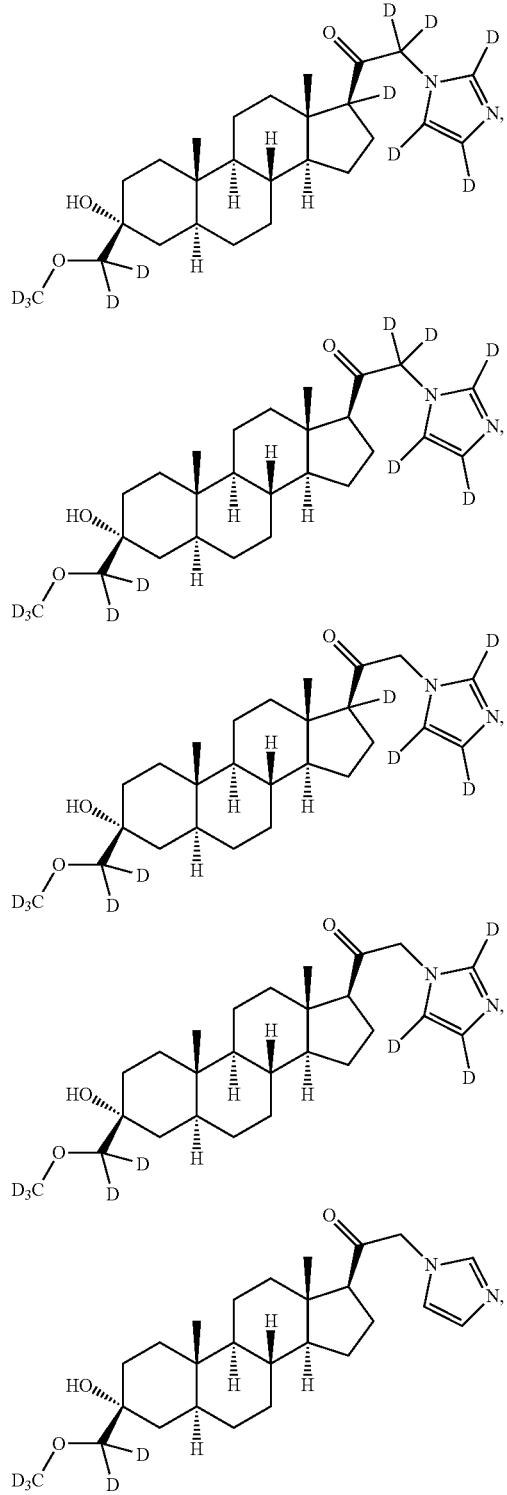

7
-continued
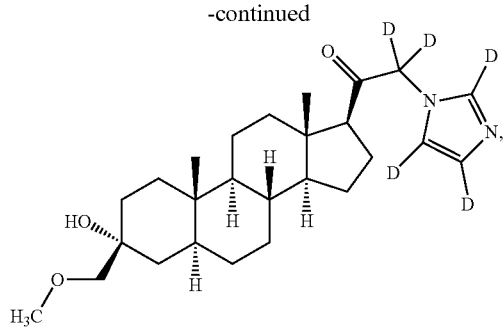
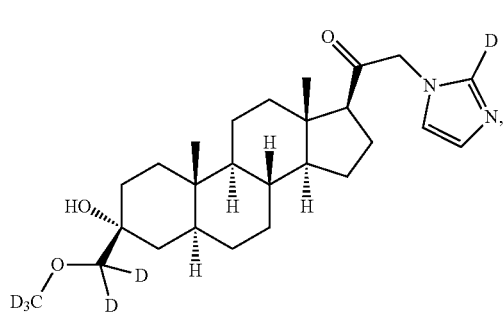
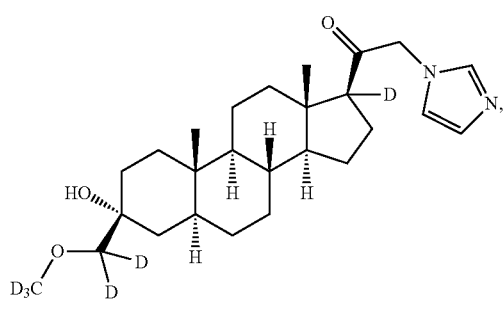
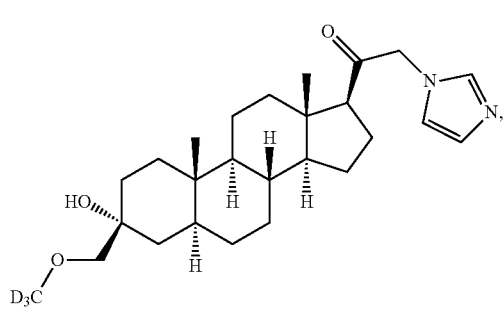
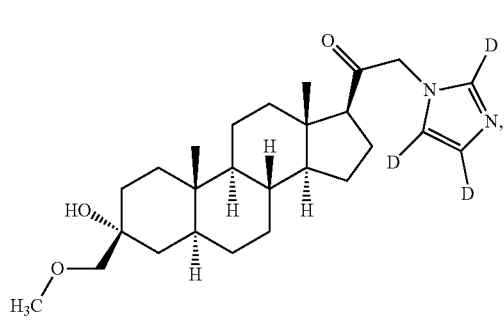
8
-continued
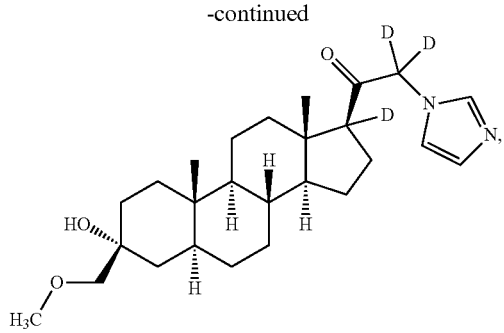
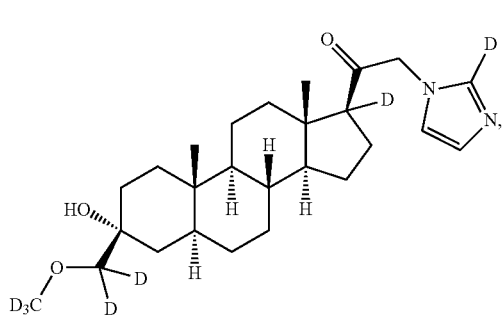
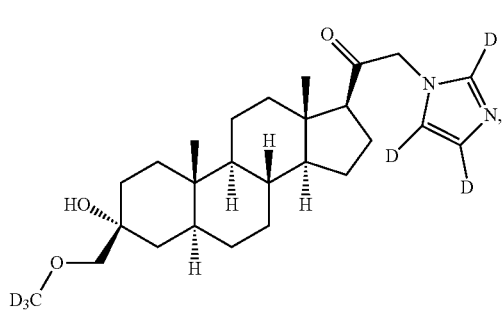
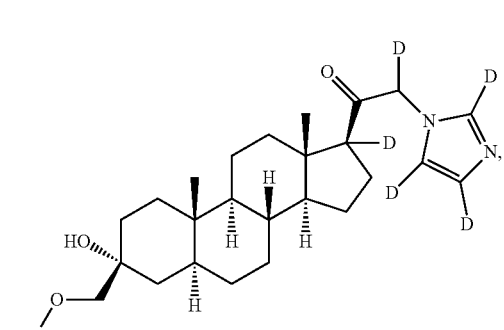
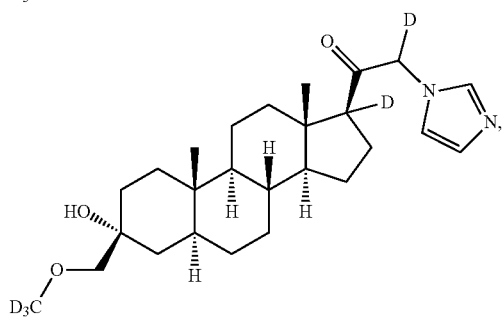

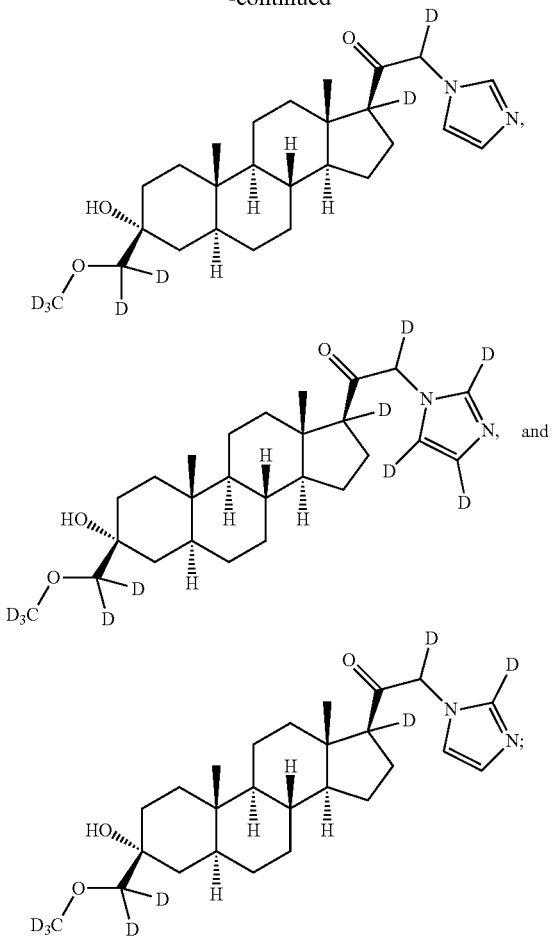

1.25 Compound I, or any of 1.1-1.24, in free form (free base form);
1.26 Compound I, or any of 1.1-1.24 in salt form, e.g., pharmaceutically acceptable salt form (e.g., hydrochloride);
1.27 Compound I or any of 1.1-1.24 in solid form;
1.28 Compound I or any of 1.1-1.27, in substantially pure diastereomeric form (i.e., substantially free from other diastereomers);
1.29 Compound I or any of 1.1-1.28 having a diastereomeric excess of greater than 70%, preferably greater than 80%, more preferably greater than 90% and most preferably greater than 95%;
1.30 Compound I or any of 1.1-1.28, having greater than 50% incorporation of deuterium at one or more of the indicated positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.
1.31 Compound I or any of 1.1-1.30 in isolated or purified form.

In a second aspect, the present disclosure provides a pharmaceutical composition (Pharmaceutical Composition 2) comprising a compound of Formula I, e.g., Compound 1 or any of 1.1-1.31, e.g., in admixture with a pharmaceutically acceptable diluent or carrier. The present disclosure provides additional exemplary embodiments of Pharmaceutical Composition 2, including:

2.1 Pharmaceutical Composition 2, wherein the Compound of Formula I et seq. is in solid form;
2.2 Pharmaceutical Composition 2 or 2.1, wherein the Composition is an immediate-release composition;
2.3 Pharmaceutical Composition 2 or 2.1, wherein the Composition is a delayed-release composition;
2.4 Pharmaceutical Composition 2 or 2.1, wherein the Composition is a sustained-release composition;
2.5 Pharmaceutical Composition 2 or any of 2.1-2.4, wherein the Composition is an oral dosage form (e.g., a tablet or capsule);
2.6 Pharmaceutical Composition 2.5, wherein the Composition is a sublingual, buccal, and/or orally-dissolvable tablet;
2.7 Pharmaceutical Composition 2 or any of 2.1-2.4, wherein the Composition is an injectable composition (e.g., formulated for intravenous, subcutaneous or intramuscular injection);
2.8 Pharmaceutical Composition 2.7, wherein the composition is a sustained release injectable composition (e.g., depot formulation), for example, formulated as a long-acting injectable for intramuscular or subcutaneous injection);
2.9 Pharmaceutical Composition 2, or any of 2.1-2.4, wherein the Composition is a transmucosal composition, e.g., a buccal, sublingual, intranasal, or pulmonary aerosol composition;
2.10 Pharmaceutical Composition 2, or any of 2.1-2.4, wherein the Composition is an ophthalmologic composition, e.g., a topical or intra-ocular injectable composition;
2.11 Pharmaceutical Composition 2, or any of 2.1-2.10, wherein the compound of Formula I et seq. is in a polymeric matrix.

Pharmaceutical Compositions 2 et seq. include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for insomnia. For intramuscular injection, the dose is generally about one-half of the oral dose.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its salt.

The pharmaceutical compositions of the present invention may be administered by any means that achieve their intended purpose. For example, administration may be by parenteral, sublingual, subcutaneous, intravenous, intramuscular, intraperitoneal, intranasal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Therapeutic plasma levels of Compound 1 et seq. can range from about 5 ng/mL to about 500 ng/mL. Other effective therapeutic ranges include from about 50 ng/mL to about 500 ng/mL, from about 50 ng/mL to about 400 ng/mL, from about 50 ng/mL to about 325 ng/mL, from about 50 ng/mL to about 250 ng/mL, from about 50 ng/mL to about 100 ng/mL, and from about 100 ng/mL to about 250 ng/mL.

In some embodiments, the Pharmaceutical Compositions of the present disclosure are injectable compositions for a sustained or delayed release, e.g., depot formulations.

In some embodiments, the Pharmaceutical Compositions comprise the Compound of Formula 1 et seq. in a polymeric matrix. In one embodiment, the Compound of the present disclosure is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 65:35, PLGA 75:25, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly (lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Compositions of the present disclosure, for example the depot composition of the present disclosure is formulated for administration by injection.

In a third aspect, the present disclosure provides a method (Method 3) for the treatment or prophylaxis of a central nervous system disorder amenable to amelioration using a $GABA_A$ receptor modulator (e.g., a positive allosteric modulator of the $GABA_A$ receptor), wherein the methods comprise the administration to a patient in need thereof of a compound of Formula I, e.g., Compound 1 or any of 1.1-1.31, or a pharmaceutical composition thereof, e.g., Composition 2 or any of 2.1-2.11. In further embodiments, the present disclosure provides:

3.1 Method 3, comprising administering Compound 1 or any of 1.1-1.31, in free or pharmaceutically acceptable salt form;

3.2 Method 3, comprising administering Pharmaceutical Composition 2 or any of 2.1-2.11;

3.3 Method 3 or any of Methods 3.1-3.2, wherein the central nervous system disorder is amenable to treatment using a positive allosteric modulator of the $GABA_A$ receptor;

3.4 Method 3.3, wherein the central nervous system disorder is selected from a group consisting of sleep disorders (e.g., insomnia), circadian rhythm disorders, phase shift disorders (e.g., jet lag), anxiety (including general anxiety, social anxiety, and panic disorders), post-traumatic stress disorder, depression (for example refractory depression, major depressive disorder, bipolar depression, postpartum depression, seasonal affective disorder, dysthymia, treatment-resistant depression, suicidal ideation or suicidal behavior, and premenstrual dysphoric disorder), compulsive disorders (e.g., obsessive-compulsive disorder), schizophrenia, schizoaffective disorder, attention disorders (e.g., attention-deficit disorder (ADD), attention deficit-hyperactivity disorder (ADHD)), convulsive disorders (e.g., seizure disorders, epilepsy or status epilepticus, including early status epilepticus, established status epilepticus, refractory status epilepticus, supra-refractory status epilepticus, and non-convulsive status epilepticus, such as generalized status epilepticus and complex partial status epilepticus), disorders of aggression (e.g., acute or chronic aggression), agitation disorders (e.g., acute or chronic agitation), disorders of memory and/or cognition (such as neurodegenerative disorders, Alzheimer's disease, senility, Lewy body dementia, vascular dementia), movement disorders (such as Parkinson's disease, Huntington's disease, tremors), autism and autism spectrum disorders (such as Asperger's syndrome), pain disorders (e.g., neuropathic pain, acute pain, chronic pain), personality disorders (e.g., anti-social personality disorder, depressive personality disorder), vascular disorders (e.g., stroke, ischemia, vascular malformations), eating disorders (e.g., bulimia, anorexia, binge-eating disorder, cachexia), traumatic brain injury, substance abuse disorders, substance use disorders, substance withdrawal syndromes, Rett Syndrome, Fragile X Syndrome, Angelman Syndrome, and tinnitus, and neurodegenerative diseases (e.g., Alzheimer's, amyotrophic lateral sclerosis, coma, dementias, Parkinson's disease, Huntington's disease, dyskinesias, dystonias); as well as any disorders requiring sedation or anesthesia for effective treatment;

3.5 Method 3.4, wherein the central nervous system disorder is selected from a group consisting of sleep disorders (e.g., insomnia), anxiety (including general anxiety, social anxiety, and panic disorders), post-traumatic stress disorder, depression (for example refractory depression, major depressive disorder, bipolar depression, postpartum depression), and convulsive disorders (e.g., seizure disorders, epilepsy or status epilepticus);

3.6 Method 3.5, wherein the central nervous system disorder is selected from a group consisting of sleep disorders (e.g., insomnia), anxiety (including general anxiety, social anxiety, and panic disorders), depression (for example refractory depression, major depressive disorder, bipolar depression, postpartum depression), and convulsive disorders (e.g., seizure disorders, epilepsy or status epilepticus);

3.7 Method 3 or any of 3.1-3.6, wherein the Compound or Composition is administered orally;

3.8 Method 3.7, wherein the Composition administered is a solid oral dosage form (e.g., a tablet or capsule);

3.9 Method 3.7, wherein the solid oral dosage form is a sublingual or buccal orally-dissolvable tablet;

3.10 Method 3 or any of 3.1-3.6, wherein the Compound or Composition is administered intranasally or by pulmonary inhalation, e.g., in the form of an aerosol;

3.11 Method 3 or any of 3.1-3.6, wherein the Compound or Composition is administered ophthalmologically, e.g., as a topical ophthalmic;

3.12 Any of Methods 3.7-3.11, wherein the Compound or Composition is administered three times per day, or twice per day, or once per day;

3.13 Method 3 or any of 3.1-3.6, wherein the Compound or Composition is administered by injection, e.g., by intravenous, subcutaneous, intra-ocular, intra-peritoneal, or intramuscular injection;

3.14 Method 3.13, wherein the Compound or Composition is administered as a long-acting injectable composition, e.g., a depot formulation;

3.15 Method 3.13 or 3.14, wherein the injection is administered once per day or once every two days, or once every three to seven days, or once per week, or once every one to four weeks, or once per month.

Other diseases and disorders amenable to treatment using the $GABA_A$ modulators of the present disclosure include those disclosed and described in US 2017/0240589, the contents of which is hereby incorporated by reference in its entirety.

Compounds of the present invention, as described herein, are generally designed to modulate GABA function, and therefore to act as neuroactive steroids for the treatment and prevention of CNS-related conditions in a subject. Modulation, as used herein, refers to the inhibition or potentiation of GABA receptor function, and in particular, positive allosteric modulation (potentiation) of $GABA_A$ receptor function. Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In another embodiment, the present disclosure provides any of Methods 3.1-3.15, wherein the method comprises administration of Pharmaceutical Composition 2 or any of 2.1-2.11, which is formulated for delayed-release and/or sustained-release of the Compounds of the Invention over a period of from about 14 days, about 30 to about 180 days, preferably over the period of about 30, about 60 or about 90 days. Delayed- and/or sustained-release is particularly useful for circumventing premature discontinuation of therapy, particularly for drug therapy where non-compliance or non-adherence to medication regimes is a common occurrence.

In still another embodiment, the invention provides any Method 3 or 3.1-3.15 as hereinbefore described, wherein the method comprises administration of a pharmaceutical composition which is a depot composition of the present disclosure, administered for controlled- and/or sustained-release of the Compounds of the Invention over a period of time.

In a fourth aspect, the present disclosure provides a method (Method 4) of inducing sedation or anesthesia in a patient in need thereof, wherein the method comprises the administration of a compound of Formula I, e.g., Compound 1 or any of 1.1-1.31, or a pharmaceutical composition thereof, e.g., Composition 2 or any of 2.1-2.11, to a patient in need thereof. In further embodiments, the fourth aspect provides:

4.1 Method 4, wherein the dose administered is effective to produce sedation and/or anesthesia in the patient within 2 hours of administration, e.g., within 1 hour of administration;

4.2 Method 4, wherein the dose administered is effective to produce sedation and/or anesthesia in the patient within 45 minutes of administration, e.g., within 30 minutes, or within 20 minutes or within 10 minutes, of administration;

4.3 Method 4, wherein the dose administered is effective to produce sedation and/or anesthesia in the patient within 5 minutes of administration, e.g., within 3 minutes, or within 2 minutes or within 1 minute, of administration;

4.4 Method 4 or any of 4.1-4.3, wherein the sedation and/or anesthesia provided by a single dose has a duration of 1 hour to 24 hours, e.g., 1 hour to 12 hours, or 1 hour to 6 hours, or 1 hour to 4 hours, or 1 hour to 2 hours;

4.5 Method 4 or any of 4.1-4.4, wherein the Compound or Composition is administered orally;

4.6 Method 4.5, wherein the Composition administered is a solid oral dosage form (e.g., a tablet or capsule);

4.7 Method 4.6, wherein the solid oral dosage form is a sublingual or buccal orally-dissolvable tablet;

4.8 Method 4 or any of 4.1-4.4, wherein the Compound or Composition is administered intranasally or by pulmonary inhalation, e.g., in the form of an aerosol;

4.9 Method 4 or any of 4.1-4.4, wherein the Compound or Composition is administered by injection, e.g., by intravenous, subcutaneous, intra-peritoneal, or intramuscular injection.

The Compounds of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the present disclosure may be simultaneously, sequentially, or contemporaneously administered with one or more anti-depressant agents, anti-psychotic agents, sedative/hypnotic agents (e.g., benzodiazepines, anti-seizure agents, substance abuse treatment agents (e.g., methadone, naloxone) and/or agents use to treat Parkinson's disease or mood disorders. In another example, side effects may be reduced or minimized by administering a Compound of the present disclosure in combination with one or more second therapeutic agents in free or salt form, wherein the dosages of (i) the second therapeutic agent(s) or (ii) both Compound of the present disclosure and the second therapeutic agents, are lower than if the agents/compounds are administered as a monotherapy.

In some embodiments, the present disclosure therefore provides Method 3, or any of Methods 3.1-3.15, or Method 4 or any of 4.1-4.9, further comprising the administration of one or more therapeutic agents to the patient, wherein the one or more therapeutic agents is selected from compounds that modulate GABA activity (e.g., enhances the activity and facilitates GABA transmission), a GABA-B agonist, a 5-HT receptor modulator (e.g., a $5-HT_{1A}$ agonist, a $5-HT_{2A}$ antagonist, a $5-HT_{2A}$ inverse agonist, a serotonin reuptake inhibitor, etc.), a melatonin receptor agonist, an ion channel modulator (e.g., blocker), a serotonin-2 receptor antagonist/reuptake inhibitor (a compound having both $5-HT_2$ antagonism and serotonin reuptake inhibition, i.e., SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, other neuroactive steroids, progesterone or progesterone metabolites, a neurokinin-1 drug, an anti-depressant, and opiate agonist and/or partial opiate agonist (such as a mu-, kappa- or delta-opiate receptor agonist or partial agonist), nociceptin agonist, an inhibitor of drug metabolism, and an antipsychotic agent, e.g., an atypical antipsychotic agent, in free or pharmaceutically acceptable salt form. In some embodiments, such agents include inhibitors of drug metabolism, such as reductase inhibitors, oxidoreductase inhibitors, or cytochrome oxidase (CYP enzyme) inhibitors which would serve to reduce the rate of metabolism of the Compound of the present disclosure being administered. For example, such agents could include inhibitors of ketone reductases and steroid hydrogenases (e.g., 20α-hydroxysteroid hydrogenase or 20β-hydroxysteroid hydrogenase). In addition to inhibitors of such reductases, oxidoreductases and hydrogenases, such inhibitors of drug metabolism could also include competitive substrates for these enzymes.

In some embodiments, the combination of a Compound of the present disclosure and one or more second therapeutic agents as described hereinbefore may be administered to the patient as a Pharmaceutical Composition or a depot Composition as hereinbefore described. The combination compositions may include mixtures of the combined drugs, as well as two or more separate compositions of the drugs, which individual compositions can be, for example, co-administered together to a patient.

In a fifth aspect, the present disclosure provides use of a compound of Formula I, e.g., Compound 1 or any of 1-1.31, or a pharmaceutical composition thereof, e.g., Composition 2 or any of 2.1-2.11, in the manufacture of a medicament for the treatment or prophylaxis of one or more disorders as disclosed hereinbefore, e.g., in any of Method 3, or any of Methods 3.1-3.15, or in the induction of sedation or anesthesia, e.g., in any of Method 4 or any of 4.1-4.9, or any other method embodiments described herein.

In a sixth aspect, the present disclosure provides use of a compound of Formula I, e.g., Compound 1 or any of 1-1.31, or a pharmaceutical composition thereof, e.g., Composition 2 or any of 2.1-2.11, in the treatment or prophylaxis of one or more disorders as disclosed hereinbefore, e.g., in any of Method 3, or any of Methods 3.1-3.15, or in the induction of sedation or anesthesia, e.g., in any of Method 4 or any of 4.1-4.9, or any other method embodiments described herein.

Without being bound by theory, the current invention provides compounds which specifically limit, slow, alter and/or prevent the metabolism which has been found to occur in animals and/or humans treated with the Compound of Formula A:

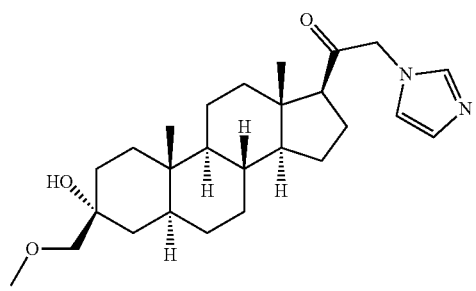

Formula A

Due to the very similar chemical and physical properties of deuterium ($^2$H) atoms compared to normal hydrogen atoms ($^1$H), e.g., atomic charge, atomic volume, polarity, valency, etc., drug compounds in which deuterium is substituted for hydrogen are believed to generally have similar biological activity to the non-deuterated analog, but potentially with improved pharmacokinetic properties. It is particularly important that while deuterium atoms have almost double the atomic mass of protium atoms, their space volume and charge distribution are similar, these latter factors being critical in binding to biological molecules. Improved pharmacokinetic properties results from the significantly higher bond strength of a C-D bond compared to an H-D bond, and consequently, the higher energy barrier to D/H abstraction during an enzymatic (metabolic) reaction (the kinetic isotope effect). The extent to which such a substitution will result in an improvement of pharmacokinetic properties without a too severe loss in pharmacologic activity is variable. Thus, in some circumstances, the resulting deuterated compound yields only a moderate increase in pharmacokinetic stability, while in other circumstances, the resulting deuterated compound may have significantly improved metabolic stability. Moreover, it may be difficult to predict with certainty the effects of simultaneous deuterium substitutions. These may or may not result in additive (synergistic) improvement in metabolic stability.

Although many deuterated pharmaceutical compounds have been proposed and explored to date, only one deuterated pharmaceutical compound has been approved by the U.S. Food and Drug Administration, deutetrabenazine (Teva Pharmaceuticals, April 2017), a deuterated version of the Huntington's disease drug tetrabenazine, which has a therapeutically useful longer half-life than its non-deuterated counterpart.

In some embodiments, the present disclosure provides compounds containing deuterium atoms at specific selected positions of the structure of compound of Formula A. These particular deuterations are expected to have in impact on metabolic degradation and clearance of said compounds because of their relationship to enzymatic pathways determined by the inventors to likely affect these compounds. These novel compounds are therefore expected to display substantially the same pharmacologic activity as the compound of Formula A, yet with unexpectedly improved metabolic stability and pharmacokinetic properties.

In other embodiments, the present disclosure provides compounds which are analogs of the compound of Formula A having biologically labile functional groups positioned within the compounds such that natural metabolic activity will remove the labile functional groups, resulting in the Compound of Formula A in vivo. As such, administration of some compounds of the present disclosure to a patient in need thereof result in a both an immediate and delayed release to the tissues of said person the Compound of Formula A. It is expected that such compounds of the present disclosure do not have significant pharmacologic activity in themselves, but will serve as a reservoir of the pharmacologically active compound of Formula A. In this way, the compounds of the present disclosure are particularly suited to formulation as long-acting injectable (LAI) or "Depot" pharmaceutical compositions. Without being bound by theory, an injected "depot" comprising a compound of the present disclosure will gradually release into the body tissues said compound, in which tissues said compound will be gradually metabolized to yield the compound of Formula A. Such depot formulations may be further adjusted by the selection of appropriate components to control the rate of dissolution and release of the compounds of the present disclosure.

"Alkyl" as used herein is a saturated or unsaturated hydrocarbon moiety, e.g., one to twenty-one carbon atoms in length, unless indicated otherwise; any such alkyl may be linear or branched (e.g., n-butyl or tert-butyl), preferably linear, unless otherwise specified. For example, "$C_{1-21}$ alkyl" denotes alkyl having 1 to 21 carbon atoms. In one embodiment, alkyl is optionally substituted with one or more hydroxy or $C_{1-22}$alkoxy (e.g., ethoxy) groups. In another embodiment, alkyl contains 1 to 21 carbon atoms, preferably straight chain and optionally saturated or unsaturated, for example in some embodiments wherein $R_1$ is an alkyl chain containing 1 to 21 carbon atoms, preferably 6-15 carbon atoms, 16-21 carbon atoms, e.g., so that together with the —C(O)— to which it attaches, e.g., when cleaved from the compound of Formula I, forms the residue of a natural or unnatural, saturated or unsaturated fatty acid.

The term "D" or "deuterium" refers to the $^2$H-isotope of the atom hydrogen. The natural abundance of the two stable isotopes of hydrogen are about 99.98% protium ($^1$H), and 0.02% deuterium ($^2$H). Thus, on average, any hydrogen atom in a molecule synthesized using common reagents will have approximately 0.02% deuterium at every hydrogen atom position. Thus, the skilled artisan would understand that when reference is made to a chemical structure having a C-D bond or a "D" atom, as described herein, this means that said position of the molecule is enriched to have more than the natural 0.02% abundance of deuterium. Thus, a label "D" in a molecule indicates, e.g., at least 0.1% deuterium, or at least 1% deuterium, or at least 10% deuterium. Preferably, any compound according to the present disclosure has greater than 50% incorporation of deuterium at each specified "D" atom position of the compound's structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan.

Unless otherwise indicated, the Compounds of the present disclosure, e.g., Compound I or 1.1-1.31 may exist in free or salt, e.g., as acid addition salts, form. An acid-addition salt of a compound of the invention which is sufficiently basic, for example, an acid-addition salt with, for example, an inorganic or organic acid, for example hydrochloric acid, and the like.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included within the scope of the compounds of the present disclosure.

The Compounds of the present disclosure may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium, $^{13}$C, $^{15}$N, $^{18}$O. Alternatively, unstable isotopes, which are radioactive isotopes which contain additional neutrons compared to the abundant nuclides of the same species (i.e., element), e.g., $^{123}$I, $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention.

Thus, in addition to the deuteration specifically provided for by the scope of the compounds of Formula I, the present disclosure further envisions compounds according to Formula I wherein one or more carbon atoms, nitrogen atoms or oxygen atoms are replaced by a stable or unstable isotopic variant (e.g., $^{11}$C, $^{13}$C, $^{15}$N, $^{18}$O), and further wherein one or more hydrogen atoms are replaced by tritium ($^3$H). These compounds are useful, e.g., for structural determinations (e.g., by nuclear magnetic resonance or mass spectral analysis) and for the purpose of radioimaging studies to elucidate metabolic and excretory pathways and to measure clearance of potential drug candidates.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylene-propylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body.

The terms "disease," "disorder," and "condition" are used interchangeably and are not intended to be interpreted with any distinction between them.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, sublingually, parenterally (intravenously, intramuscular, intranasal or subcutaneous) or transdermally, but are preferably administered orally. In certain embodiments, the Compounds of the Invention, e.g., in depot formulation, are preferably administered parenterally, e.g., by injection.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred.

Pharmaceutical compositions comprising Compounds of the present disclosure may be prepared using conventional diluents or excipients (an example include, but is not limited to sesame oil) and techniques known in the galenic art. Thus, oral dosage forms may include tablets, capsules, solutions, suspensions and the like.

Methods for the synthesis of compound of Formula A, including the intermediates therefor, have been disclosed in U.S. Publications 2004/0034002 and 2009/0131383, the contents of which are incorporated by reference in their entireties.

The essential core of other Compounds of the present disclosure came be made by analogous procedures disclosed in the above-reference publications and known to those skilled in the art. The particular deuterated compounds of the present disclosure may generally be prepared by analogous means by substituting commercially available deuterated reagents for non-deuterated reagents, when such deuterated reagents are available.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

Diastereomers of prepared compounds can be separated by, for example, HPLC using CHIRALPAK® AY-H, 5µ, 30×250 mm at room temperature and eluted with 10% ethanol/90% hexane/0.1% dimethylethylamine. Peaks can be detected at 230 nm to produce 98-99.9% ee of the diastereomer.

3α-Hydroxy-3β-methoxymethyl-5α-pregnan-20-one may be prepared from (3R)-spiro[oxirane-2α, 5α-pregnan]-20-one and sodium methoxide as described by Hogenkamp, et al., "Synthesis and in Vitro Activity of 3β-Substituted-3α-hydroxypregnan-20-ones: Allosteric Modulators of the GABA$_A$ Receptor," *J Med. Chem.* 40:61-72 (1997). 21-Substituted steroids may be prepared from the corresponding 21-bromo steroids which are synthesized from the 20-keto-steroids using Br$_2$ in MeOH with catalytic HBr. Other sources for useful synthetic methodologies include: Botella et al., *J. Med Chem.,* 48: 3500-3511 (2015); Botella et al., *J. Med Chem.,* 60: 7810-7819 (2017); Wong et al., *Steroids* 71: 77-82 (2006); Botella et al., WO 2016/061527; Hogenkamp, Derek L., WO 2000/66614; Goliber et al., US 2006/0074059; Chang et al., WO 2005/105822; and Woodward, Richard M., WO 2006/131392; the contents of each of which are hereby incorporated by reference in their entireties. Generally speaking, the compounds of the present disclosure can be made according to methods known in the art starting from the widely-known compound 3α-hydroxy-5α-pregnan-2-one, and diastereomers thereof.

For example, this compound can be prepared according to the following scheme from Wong et al.:

21
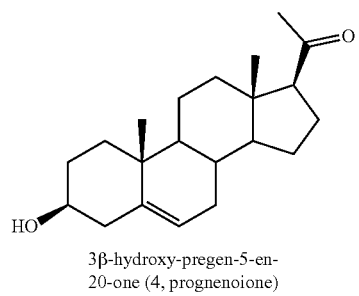
3β-hydroxy-pregen-5-en-
20-one (4, prognenoione)
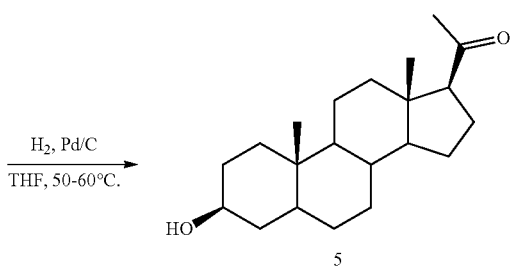
5
22
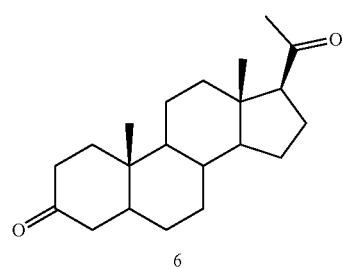
6
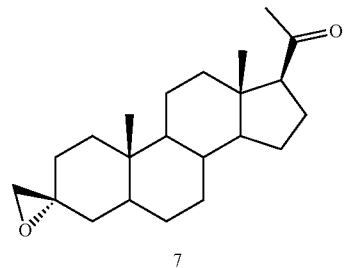
7
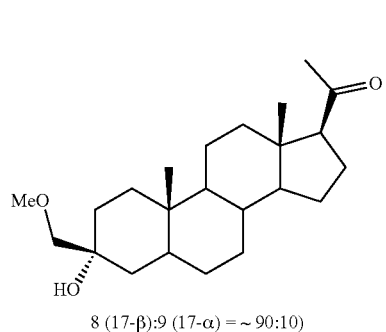
8 (17-β):9 (17-α) = ~ 90:10
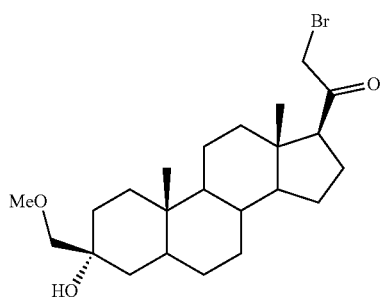
10
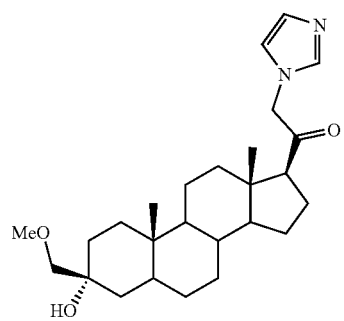
11
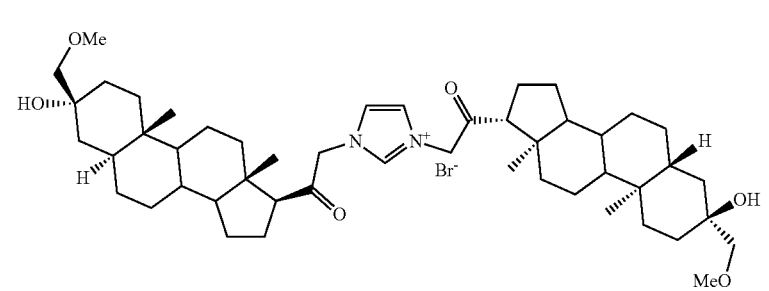
12 (1,3-disubstituted imidazolium adduct)

Example 1: Synthesis of 3α-Hydroxy-21-(1'-imidazolyl)-3β-methoxymethyl-5α-pregnan-20-one (compound of Formula A)

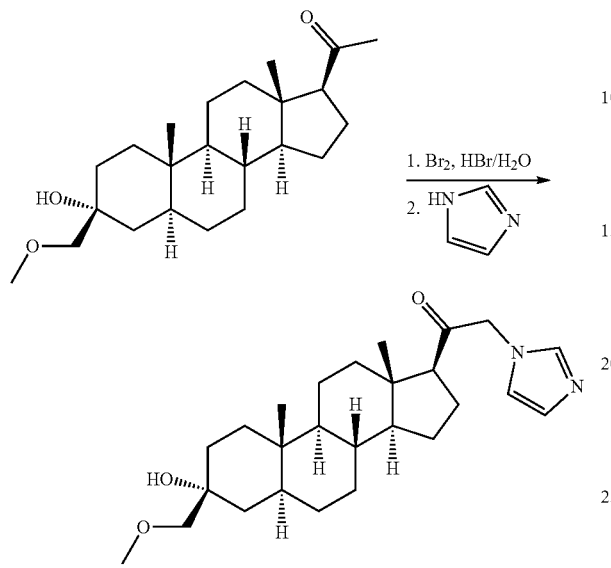

Step 1: 21-Bromo-3α-hydroxy-3β-methoxymethyl-5α-pregnan-20-one

To a solution of 3α-hydroxy-3β-methoxymethyl-5α-pregnan-20-one (30.0 g, 82.9 mmol) in 900 mL of methanol stirring at room temperature is added 3 drops of a 48% aqueous HBr solution. Bromine (13.9 g, 87.1 mmol) is then added dropwise as a solution in 200 mL of methanol over 2 hours during which the reaction was shielded from light. After TLC (1% acetone/methylene chloride) indicates the absence of starting material and the formation of a less polar product, the reaction is concentrated to approximately 300 mL. $CH_2Cl_2$ (400 mL) is then added and the reaction is poured into a separatory funnel containing 200 mL of water. The phases are separated and the aqueous phase is extracted with $CH_2Cl_2$ (3×100 mL). The organic phases are combined, washed with 200 mL of a saturated aqueous $NaHCO_3$ solution, dried over $Na_2SO_4$, and concentrated under reduced pressure to afford the bromide as a pale-yellow foam. No further purification is necessary.

Step 2: 3α-Hydroxy-21-(1'-imidazolyl)-3β-methoxymethyl-5α-pregnan-20-one

To a suspension of the bromide prepared above (36.7 g, 82.9 mmol) in 800 mL of $CH_3CN$ is added imidazole (28.2 g, 415 mmol) and the reaction is heated to reflux under argon. The reaction is complete after 1 hour at reflux (TLC, 95:4.5:0.5 $CH_2Cl_2$:MeOH:Triethylamine (TEA)). The reaction is cooled to room temperature and is then concentrated in vacuo. The resulting oil is dissolved in 600 mL of $CH_2Cl_2$, washed with a dilute $NaHCO_3$ solution (4×200 mL), dried over $Na_2SO_4$ and concentrated in vacuo. Purification via flash chromatography on silica gel eluting with 95:4.5:0.5 $CH_2Cl_2$:MeOH:TEA affords 18 g of the title compound as a white solid, mp 185-187° C. (evacuated capillary). $^1$H NMR (300 MHz, $CDCl_3$) δ 7.40 (s, 1H), 7.08 (s, 1H), 6.84 (s, 1H), 4.72 (d, 1H, J=17.7 Hz), 4.64 (d, 1H, J=18 Hz), 3.39 (s, 3H), 3.18 (s, 2H), 2.57 (t, 1H, J=8.7 Hz), 0.76 (s, 3H), 0.66 (s, 3H).

Example 2: 1-((3R,5S,8R,9S,10S,13S,14S,17S)-3-hydroxy-3-(methoxymethyl)-10,13-dimethylhexadecahydro-1H-cyclopenta[a]phenanthren-17-yl)-2-(1H-imidazol-1-yl-d3)ethan-1-one

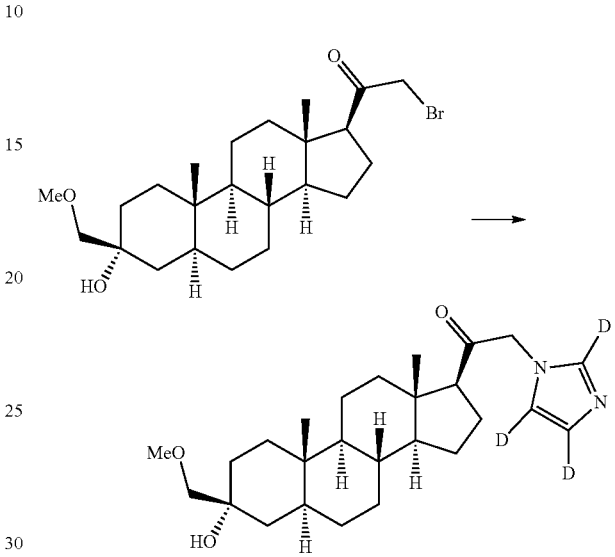

To a solution of imidazole-$d_4$ (0.193 g, 2.72 mmol, 3.0 equiv.) in THF (2 mL) at 0° C. is added lithium hydride (0.0237 g, 2.8 mmol, 3.1 equiv.). The solution is stirred at 0° C. for 2 hours under Ar. 21-Bromo-3α-hydroxy-3β-methoxymethyl-5α-pregnan-20-one (0.40 g, 0.906 mmol, 1.0 equiv.) in THF (2.5 mL) is slowly added to the reaction mixture at 0° C. over a period of 5 min under Ar. After being stirred at 0° C. for 3 hours, the reaction mixture is quenched by methanol in ice-bath. The organic layer is separated and concentrated under reduced pressure. The residue is further purified by column chromatography to give the pure title compound (0.184 g, 0.426 mmol) as white powder in 50% isolated yield. $^1$H NMR (500 MHz, Chloroform-d) δ 4.86-4.60 (m, 2H), 3.41 (s, 3H), 3.20 (s, 2H), 2.60 (t, J=8.9 Hz, 1H), 2.31-2.12 (m, 1H), 2.06-1.90 (m, 1H), 1.84-1.66 (m, 4H), 1.66-1.13 (m, 12H), 1.63-1.51 (m, 3H) 1.00 (m, 1H), 0.87 (m, 1H), 0.78 (s, 3H), 0.68 (s, 3H).

Example 3: 1-((3R,5S,8R,9S,10S,13S,14S,17S)-3-hydroxy-3-((methoxy-d3)methyl)-10,13-dimethyl-hexadecahydro-1H-cyclopenta[a]phenanthren-17-yl)-2-(1H-imidazol-1-yl)ethan-1-one

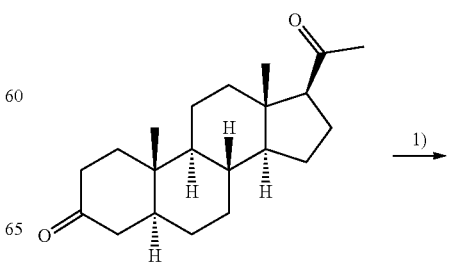

25

-continued

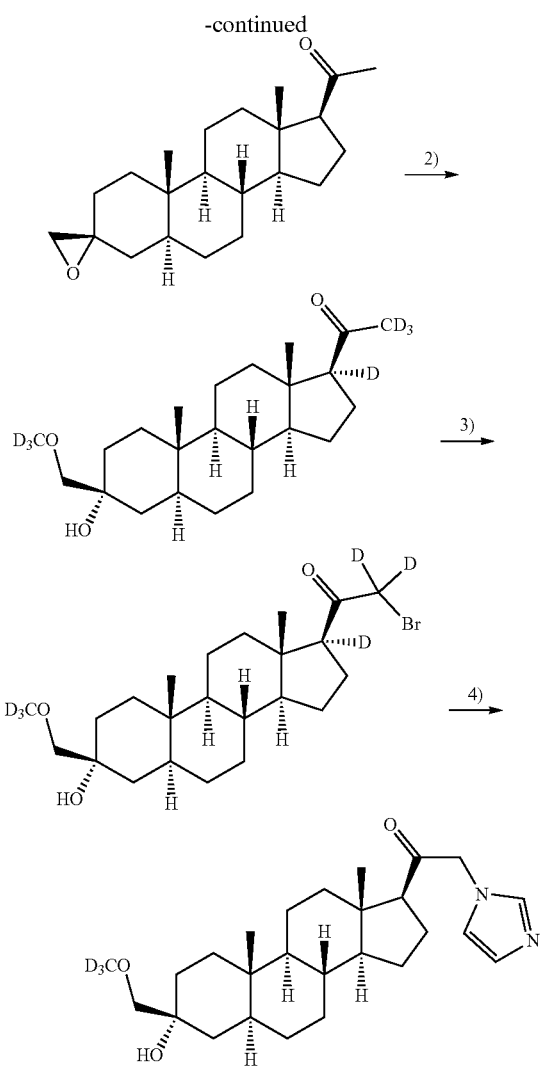

Step 1: 1-((3R,5S,8R,9S,10S,13S,14S,17S)-10,13-dimethylhexadecahydrospiro[cyclopenta[a]phenanthrene-3,2'-oxiran]-17-yl)ethan-1-one A stirred solution trimethylsulfoxonium iodide (2.09 g, 9.5 mmol) and potassium tert-butoxide (1.134 g, 10.01 mmol) in DMSO (30.0 mL) is heated at 60° C. for 1 hour under Ar. 5α-Pregnane-3,20-dione (2.0 g, 6.3 mmol) is added to the reaction mixture and stirred at room temperature for overnight. After the reaction is completed, the reaction mixture is quenched and precipitated by water (30 mL) in ice-bath. The resultant precipitate is collected by filtration, washed with water (50 mL×2). The residue is purified by recrystallization from MeOH/acetone (4/1), then the solid is dried under vacuum overnight to give pure final product (1.83 g, 5.54 mmol) as a white powder in 87% yield. $^1$H NMR (500 MHz, Chloroform-d) δ 2.64 (d, J=1.4 Hz, 2H), 2.56 (t, J=8.9 Hz, 1H), 2.25-2.15 (m, 1H), 2.14 (s, 3H), 2.11-1.99 (m, 2H), 1.89 (t, J=14.0, 13.1 Hz, 1H), 1.79-1.60 (m, 6H), 1.60-1.51 (m, 1H), 1.50-1.05 (m, 9H), 1.06-0.94 (m, 2H), 0.90 (s, 3H), 0.63 (s, 3H).

Step 2: 1-((3R,5S,8R,9S,10S,13S,14S,17S)-3-hydroxy-3-((methoxy-d3)methyl)-10,13-dimethylhexadecahydro-1H-cyclopenta[a]phenanthren-17-yl-17-d)ethan-1-one-2,2,2-d3

Sodium hydroxide (0.916 g, 22.9 mmol) is dissolved in methanol-$d_4$ (40 mL) and heated at reflux for 30 min under Ar. The compound from Step 1 (3.8 g, 11.4 mmol) is slowly added to the methanolic solution at room temperature under Ar, and the solution is heated at 40° C. for overnight. The reaction mixture is quenched and precipitated by water (65 mL) in ice-bath. The resultant precipitate is filtrated, washed with water (25 mL×2). The solid cake is further purified by recrystallization from ethyl acetate/hexanes (1/1) and dried under vacuum to give pure product (3.15 g, 8.52 mmol) as a white powder in 74% yield. $^1$H NMR (500 MHz, Chloroform-d) δ 3.20 (s, 2H), 2.26-2.13 (m, 1H), 2.04-1.95 (m, 1H), 1.80-1.51 (m, 8H), 1.52-1.12 (m, 12H), 0.98 (m 1H), 0.85 (m, 1H), 0.77 (s, 3H), 0.62 (s, 3H).

Step 3: 2-bromo-1-((3R,5S,8R,9S,10S,13S,14S,17S)-3-hydroxy-3-((methoxy-d3)methyl)-10,13-dimethylhexadecahydro-1H-cyclopenta[a]phenanthren-17-yl-17-d)ethan-1-one-2,2-d2

To a solution of the compound from step 2 (3.11 g, 8.41 mmol) in MeOH (30 mL) is added three drops of aqueous HBr solution (48%). Bromine (0.485 mL, 8.88 mmol) is dissolved in MeOH (20 mL) and added dropwise to the reaction mixture in the dark. After the reaction is completed, the reaction mixture is quenched by water (100 mL). Ethyl acetate (30 mL×3) is added to extract the final product, combined the organic phase and washed again with water (20 mL×2). Evaporated the solvent and dried under vacuum for overnight to give pure 7 (3.67 g, 8.20 mmol) as white powder in 97% yield. $^1$H NMR (500 MHz, Chloroform-d) δ 3.20 (s, 2H), 2.19 (t, J=10.8 Hz, OH), 1.92 (ddd, J=11.9, 4.1, 2.9 Hz, 1H), 1.79-1.51 (m, 7H), 1.51-1.15 (m, 12H), 1.06-0.93 (m, 1H), 0.89-0.80 (m, 1H), 0.77 (s, 3H), 0.65 (s, 3H).

Step 4: 1-((3R,5S,8R,9S,10S,13S,14S,17S)-3-hydroxy-3-((methoxy-d3)methyl)-10,13-dimethylhexadecahydro-1H-cyclopenta[a]phenanthren-17-yl)-2-(1H-imidazol-1-yl)ethan-1-one To a solution of imidazole (0.274 g, 4.03 mmol, 3.0 equiv.) in THF (2 mL) is added lithium hydride (0.035 g, 4.17 mmol, 3.1 equiv.). The solution is heated at reflux for 30 min under Ar. The compound from Step 3 (0.6 g, 1.34 mmol, 1.0 equiv.) in THF (4 mL) is slowly added to the reaction mixture at 0° C. over a period of 5 min under Ar. After being stirred at 0° C. for 3 hours, the reaction mixture is quenched by methanol in ice-bath. Evaporated the solvent and purified by column chromatography to give the title compound (0.12 g, 0.277 mmol) as white powder in 21% isolated yield. $^1$H NMR (500 MHz, Chloroform-d) δ 7.39 (s, 1H), 7.13 (s, 1H), 6.88 (s, 1H), 4.93-4.56 (m, 2H), 3.20 (s, 1H), 2.60 (t, J=8.8 Hz, 1H), 2.33-2.12 (m, 1H), 1.98 (dt, J=11.8, 3.3 Hz, 1H), 1.83-1.66 (m, 4H), 1.63-1.54 (m, 4H), 1.51-1.13 (m, 12H), 1.07-0.94 (m, 1H), 0.91-0.82 (m, 1H), 0.78 (s, 3H), 0.68 (s, 3H).

Example 4: 1-((3R,5S,8R,9S,10S,13S,14S,17S)-3-hydroxy-3-((methoxy-d3)methyl)-10,13-dimethyl-hexadecahydro-1H-cyclopenta[a]phenanthren-17-yl)-2-(1H-imidazol-1-yl-d3)ethan-1-one

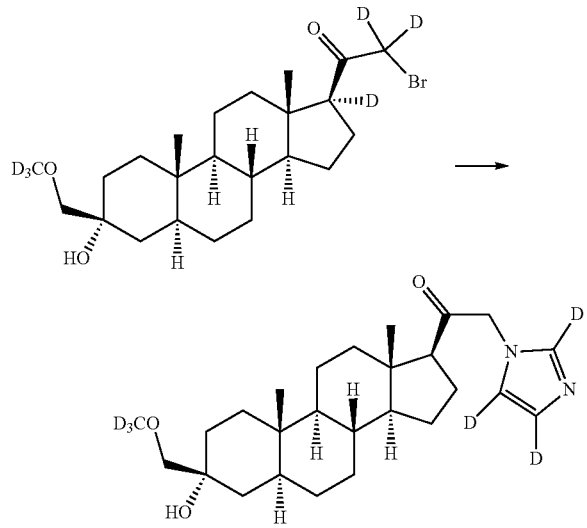

To a solution of imidazole-d4 (0.291 g, 4.03 mmol, 3.0 equiv.) in THF (2 mL) is added lithium hydride (0.035 g, 4.17 mmol, 3.1 equiv.). The solution is heated at reflux for 30 min under Ar. The compound from Example 3 Step 3 (0.6 g, 1.34 mmol, 1.0 equiv.) in THF (4 mL) is slowly added to the reaction mixture at 0° C. over a period of 5 min under Ar. After being stirred at 0° C. for 3 hours, the reaction mixture is quenched by methanol in ice-bath. Evaporated the solvent and purified by column chromatography to give the pure title compound (0.07 g, 0.016 mmol) as white powder in 12% isolated yield. $^1$H NMR (500 MHz, Chloroform-d) δ 3.20 (s, 2H), 2.60 (t, J=8.9 Hz, 1H), 2.31-2.15 (m, 1H), 2.08-1.90 (m, 1H), 1.82-1.66 (m, 4H), 1.64-1.14 (m, 15H), 1.08-0.93 (m, 1H), 0.92-0.83 (m, 1H), 0.78 (s, 3H), 0.68 (s, 3H).

Example 5: 1-((3R,5S,8R,9S,10S,13S,14S,17S)-3-hydroxy-3-((methoxy-d3)methyl)-10,13-dimethyl-hexadecahydro-1H-cyclopenta[a]phenanthren-17-yl-17-d)-2-(1H-imidazol-1-yl)ethan-1-one-2-d

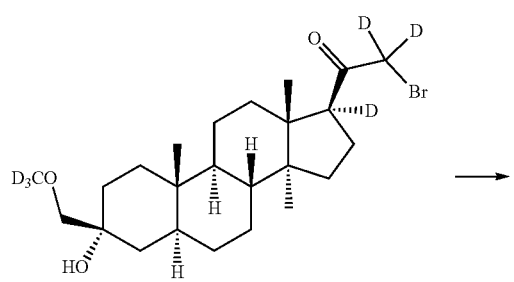

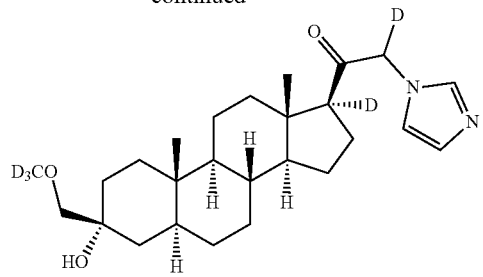

To a solution of imidazole (0.161 g, 2.37 mmol, 3.0 equiv.) in THF (2 mL) is added lithium hydride (0.021 g, 2.45 mmol, 3.1 equiv.). The solution is stirred at 0° C. for 2 hours under Ar. The compound from Example 3 Step 3 (0.353 g, 0.79 mmol, 1.0 equiv.) in THF (2.5 mL) is slowly added to the reaction mixture at 0° C. over a period of 5 min under Ar. After being stirred at 0° C. for 3 hours, the reaction mixture is quenched by D$_2$O (1.5 mL) in ice-bath. Evaporated the solvent and purified by column chromatography to give the pure title compound (0.097 g, 0.253 mmol) as white powder in 29% isolated yield. $^1$H NMR (500 MHz, Chloroform-d) δ 7.56 (s, 1H), 7.14 (s, 1H), 7.04-6.84 (m, 1H), 5.05-4.43 (m, 1H), 3.20 (s, 2H), 2.33-2.14 (m, 1H), 1.97 (dt, J=11.6, 3.4 Hz, 1H), 1.82-1.66 (m, 4H), 1.57 (m, 3H), 1.50-1.15 (m, 12H), 1.06-0.92 (m, 1H), 0.91-0.82 (m, 1H), 0.78 (s, 3H), 0.68 (s, 3H).

Example 6: 1-((3R,5S,8R,9S,10S,13S,14S,17S)-3-hydroxy-3-((methoxy-d3)methyl)-10,13-dimethyl-hexadecahydro-1H-cyclopenta[a]phenanthren-17-yl-17-d)-2-(1H-imidazol-1-yl-d3)ethan-1-one-2-d

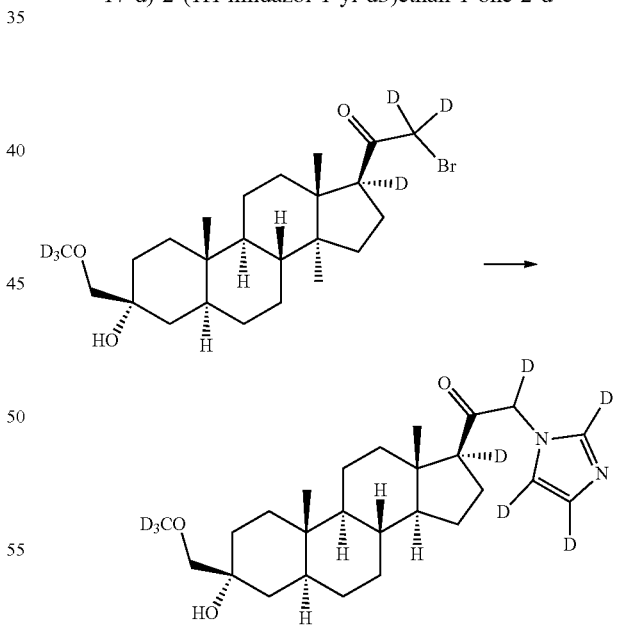

To a solution of imidazole-d4 (0.194 g, 2.69 mmol, 3.0 equiv.) in THF (2 mL) is added lithium hydride (0.023 g, 2.78 mmol, 3.1 equiv.). The solution is stirred at 0° C. for 2 hours under Ar. The compound from Example 3 Step 3 (0.4 g, 0.89 mmol, 1.0 equiv.) in THF (2.5 mL) is slowly added to the reaction mixture at 0° C. over a period of 5 min under Ar. After being stirred at 0° C. for 3 hours, the reaction mixture is quenched by D$_2$O (1.5 mL) in ice-bath. Evaporated the solvent and purified by column chromatography to give pure 11 (0.17 g, 0.389 mmol) as white powder in 44% isolated yield. $^1$H NMR (500 MHz, Chloroform-d) δ 4.92-4.38 (m, 1H), 3.20 (s, 2H), 2.36-2.06 (m, 1H), 1.97 (dt, J=11.8, 3.4 Hz, 1H), 1.85-1.63 (m, 4H), 1.64-1.14 (m, 11H), 0.99 (m, 1H), 0.86 (m, 1H), 0.78 (s, 3H), 0.68 (s, 3H).

Example 7: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl)-2-(1H-imidazol-1-yl)ethan-1-one

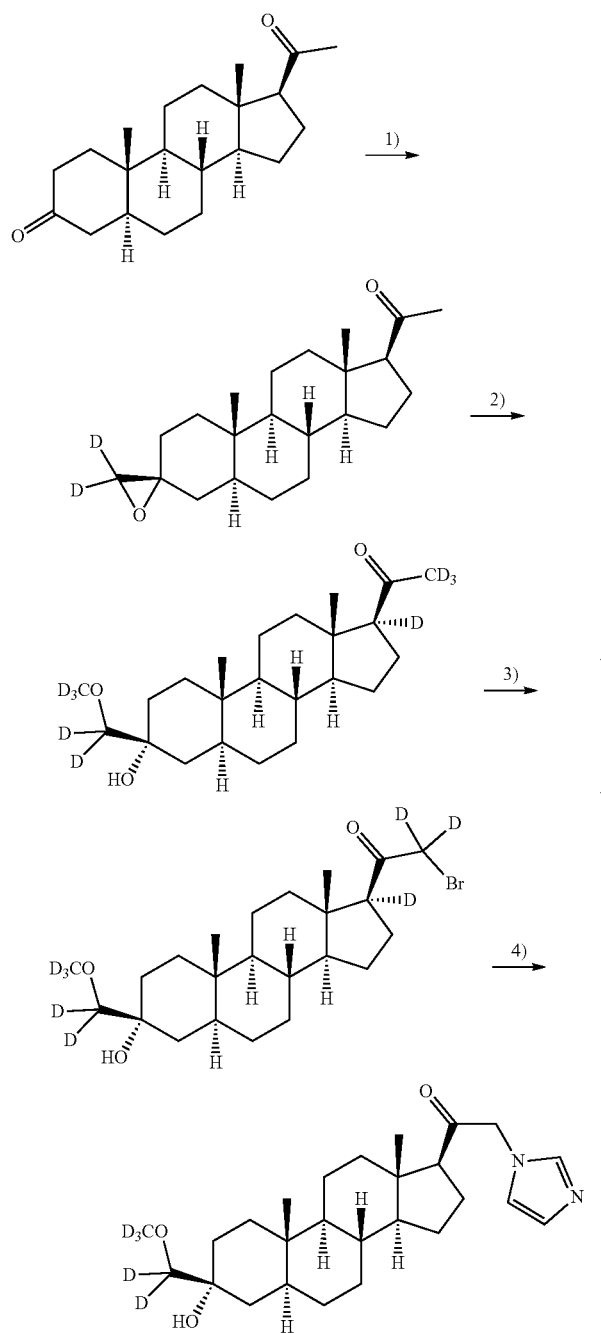

Step 1: 1-((3R,5S,8R,9S,10S,13S,14S,17S)-10,13-dimethylhexadecahydrospiro[cyclopenta[a]phenanthrene-3,2'-oxiran]-17-yl-3',3'-d2)ethan-1-one A stirred solution of trimethylsulfoxonium-d$_9$ iodide (2.17 g, 9.48 mmol) and potassium tert-butoxide (1.13 g, 10.1 mmol) in d6-DMSO (26.0 mL) is heated at 60° C. for 1 hour under Ar. 5α-Pregnane-3,20-dione (2.0 g, 6.3 mmol) is added to the reaction mixture and stirred at room temperature for overnight. After the reaction is completed, the reaction mixture is quenched and precipitated by water (60 mL) in ice-bath. The resultant precipitate is collected by filtration, washed with water (50 mL×2). The residue is further purified by recrystallization from MeOH/acetone (4/1) and dried under vacuum to give pure final product (2.08 g, 6.2 mmol) as a white powder in 99% yield and 91.5% isotopic purity. $^1$H NMR (500 MHz, Chloroform-d) δ 2.56 (t, J=9.0 Hz, 1H), 2.28-2.09 (m, 3H), 2.08-1.98 (m, 2H), 1.89 (t, J=13.5 Hz, 1H), 1.80-1.62 (m, 5H), 1.57 (m, 2H), 1.50-1.06 (m, 10H), 0.97 (m, 1H), 0.92-0.73 (m, 5H), 0.63 (s, 3H).

Step 2: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl-17-d)ethan-1-one-2,2,2-d3

Sodium hydroxide (0.49 g, 12.2 mmol) is dissolved in methanol-d$_4$ (20 mL) and heated at reflux for 30 min under Ar. The compound from Step 1 (2.04 g, 6.12 mmol) is slowly added to the methanolic solution at room temperature under Ar, and the solution is heated at 40° C. for overnight. The reaction mixture is quenched and precipitated by water (60 mL) in ice-bath. The resultant precipitate is filtrated, washed with water (25 mL×2). The solid cake is further purified by recrystallization from ethyl acetate/hexanes (1/1) and dried under vacuum to give pure product (1.43 g, 3.85 mmol) as a white powder in 63% yield. $^1$H NMR (500 MHz, Chloroform-d) δ 2.23-2.12 (m, 1H), 2.01 (dt, J=12.1, 3.4 Hz, 1H), 1.80-1.51 (m, 7H), 1.49-1.12 (m, 11H), 1.06-0.92 (m, 1H), 0.89-0.79 (m, 1H), 0.77 (s, 3H), 0.62 (s, 3H).

Step 3: 2-bromo-1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl-17-d)ethan-1-one-2,2-d2

To a solution of the compound from Step 2 (1.43 g, 3.85 mmol) in MeOH (12 mL) is added three drops of aqueous HBr solution (48%). Bromine (0.209 mL, 4.04 mmol) is dissolved in MeOH (8 mL) and added dropwise to the reaction mixture in the dark. After the reaction is completed, the reaction mixture is quenched by water (60 mL). Ethyl acetate (40 ml×2) is added to extract the final product, combined the organic phase and washed again with water (30 mL×2). Evaporated the solvent and dried under vacuum for overnight to give pure product (1.70 g, 3.78 mmol) as white powder in 98% yield. $^1$H NMR (500 MHz, Chloroform-d) δ 2.24-2.12 (m, 1H), 1.92 (dt, J=11.8, 3.5 Hz, 1H), 1.79-1.64 (m, 4H), 1.62-1.50 (m, 3H), 1.50-1.15 (m, 11H), 1.04-0.92 (m, 1H), 0.90-0.80 (m, 1H), 0.77 (s, 3H), 0.65 (s, 3H).

Step 4: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl)-2-(1H-imidazol-1-yl)ethan-1-one To a solution of imidazole (0.182 g, 2.7 mmol, 3.0 equiv.) in THF (1.5 mL) is added lithium hydride (0.023 g, 2.76 mmol, 3.1 equiv.). The solution is stirred at 0° C. for 2 hours under Ar. The compound from Step 3 (0.4 g, 0.89 mmol, 1.0 equiv.) in THF (3.0 mL) is slowly added to the reaction mixture at 0° C. over a period of 5 min under Ar. After being stirred at 0° C. for 3 hours, the reaction mixture is quenched by methanol (3.0 mL) in ice-bath. The solvent is evaporated, and the residue is purified by flash column chromatography on silica gel to give the corresponding product, then purified again by Semi-Prep HPLC to generate the final product (0.063 g, 0.145 mmol) as white powder in 16% isolated yield. $^1$H NMR (500 MHz, Chloroform-d) δ 7.49 (s, 1H), 7.13 (s, 1H), 6.88 (s, 1H), 4.97-4.45 (m, 2H), 2.60 (t, J=9.0 Hz, 1H), 2.27-2.10 (m, 1H), 1.98 (d, J=11.9, 3.4 Hz, 1H), 1.80-1.66 (m, 4H), 1.62-1.52 (m, 3H), 1.51-1.16 (m, 12H), 1.06-0.93 (m, 1H), 0.90-0.81 (m, 1H), 0.78 (s, 3H), 0.68 (s, 3H).

Example 8: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl)-2-(1H-imidazol-1-yl-2-d)ethan-1-one

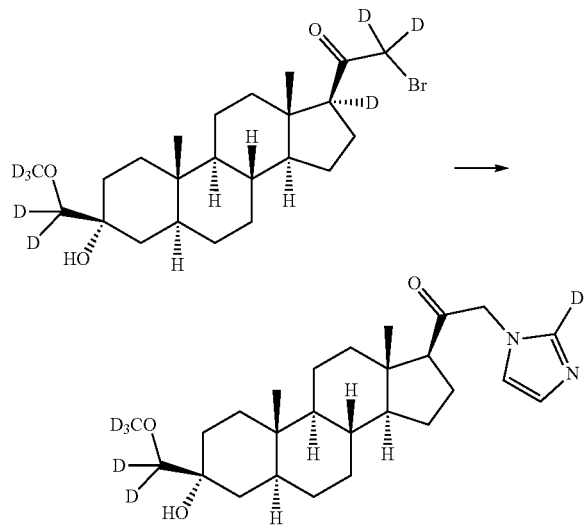

To a solution of imidazole-d1 (0.184 g, 2.67 mmol, 3.0 equiv.) in THF (2.0 mL) is added lithium hydride (0.023 g, 2.76 mmol, 3.1 equiv.). The solution is stirred at 0° C. for 2 hours under Ar. The compound of Example 7 Step 3 (0.4 g, 0.89 mmol, 1.0 equiv.) in THF (3.0 mL) is slowly added to the reaction mixture at 0° C. over a period of 5 min under Ar. After being stirred at 0° C. for 3 hours, the reaction mixture is quenched by methanol (3.0 mL) in ice-bath. The solvent is evaporated, and the residue is purified by flash column chromatography on silica gel to give the corresponding product, then purified again by Semi-Prep HPLC to generate the final product (0.163 g, 0.375 mmol) as white powder in 42% isolated yield. $^1$H NMR (500 MHz, Chloroform-d) δ 7.28 (s, 1H), 6.88 (s, 1H), 5.06-4.50 (m, 2H), 2.60 (t, J=8.9 Hz, 1H), 2.34-2.12 (m, 1H), 1.98 (dt, J=11.8, 3.4 Hz, 1H), 1.80-1.67 (m, 4H), 1.64-1.51 (m, 3H), 1.51-1.15 (m, 11H), 1.07-0.94 (m, 1H), 0.91-0.82 (m, 1H), 0.78 (s, 3H), 0.68 (s, 3H).

Example 9: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl)-2-(1H-imidazol-1-yl-d3)ethan-1-one

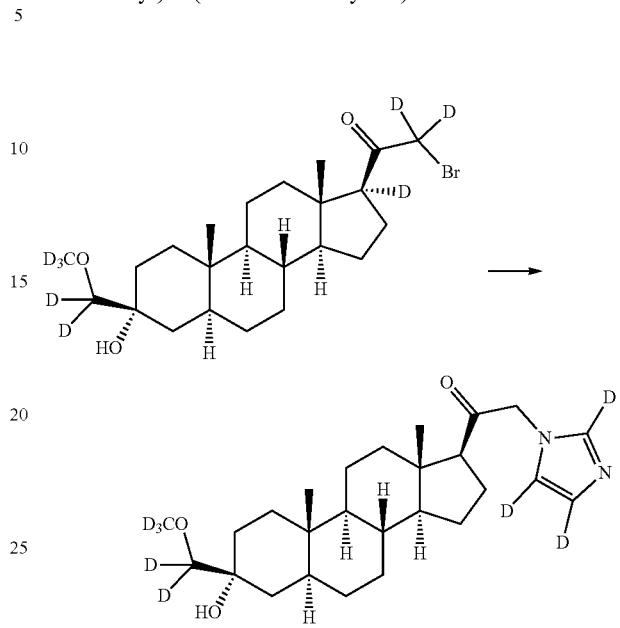

To a solution of imidazole-d4 (0.144 g, 2.00 mmol, 3.0 equiv.) in THF (2.0 mL) is added lithium hydride (0.0174 g, 2.07 mmol, 3.1 equiv.). The solution is stirred at 0° C. for 2 hours under Ar. The compound of Example 7 Step 3 (0.3 g, 0.667 mmol, 1.0 equiv.) in THF (3.0 mL) is slowly added to the reaction mixture at 0° C. over a period of 5 min under Ar. After being stirred at 0° C. for 3 hours, the reaction mixture is quenched by methanol (3.0 mL) in ice-bath. The solvent is evaporated, and the residue is purified by flash column chromatography on silica gel to give the corresponding product, then purified again by Semi-Prep HPLC to generate the final product (0.147 g, 0.337 mmol) as white powder in 51% isolated yield. $^1$H NMR (500 MHz, Chloroform-d) δ 4.87-4.36 (m, 2H), 2.60 (t, J=8.9 Hz, OH), 2.34-2.07 (m, 2H), 1.98 (dt, J=11.7, 3.4 Hz, OH), 1.80-1.65 (m, 2H), 1.64-1.52 (m, 1H), 1.51-1.15 (m, 11H), 1.06-0.94 (m, 1H), 0.90-0.82 (m, 1H), 0.78 (s, 3H), 0.68 (s, 3H).

Example 10: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl-17-d)-2-(1H-imidazol-1-yl)ethan-1-one

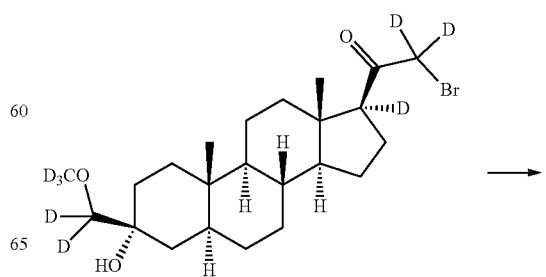

-continued

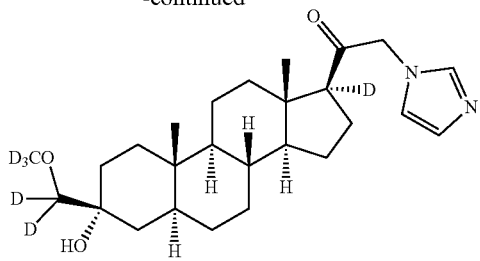

To a solution of imidazole (0.136 g, 2.00 mmol, 3.0 equiv.) in THF (2.0 mL) is added lithium hydride (0.0174 g, 2.07 mmol, 3.1 equiv.). The solution is stirred at 0° C. for 2 hours under Ar. The compound of Example 7 Step 3 (0.3 g, 0.667 mmol, 1.0 equiv.) in THF (2.5 mL) is slowly added to the reaction mixture at 0° C. over a period of 5 min under Ar. After being stirred at 0° C. for 3 hours, the reaction mixture is quenched by D$_2$O (1.50 mL) in ice-bath. The solvent is evaporated, and the residue is purified by flash column chromatography on silica gel to give the corresponding product, then purified again by Semi-Prep HPLC to generate the final product (0.140 g, 0.322 mmol) as white powder in 48% isolated yield. $^1$H NMR (500 MHz, Chloroform-d) δ 7.60 (s, 1H), 7.15 (s, 1H), 6.89 (s, 1H), 5.20-4.42 (m, 2H), 2.41-2.11 (m, 1H), 2.05-1.87 (m, 1H), 1.80-1.65 (m, 4H), 1.63-1.52 (m, 3H), 1.50-1.15 (m, 13H), 1.06-0.93 (m, 1H), 0.91-0.83 (m, 1H), 0.78 (s, 3H), 0.68 (s, 3H).

Example 11: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl-17-d)-2-(1H-imidazol-1-yl-2-d)ethan-1-one

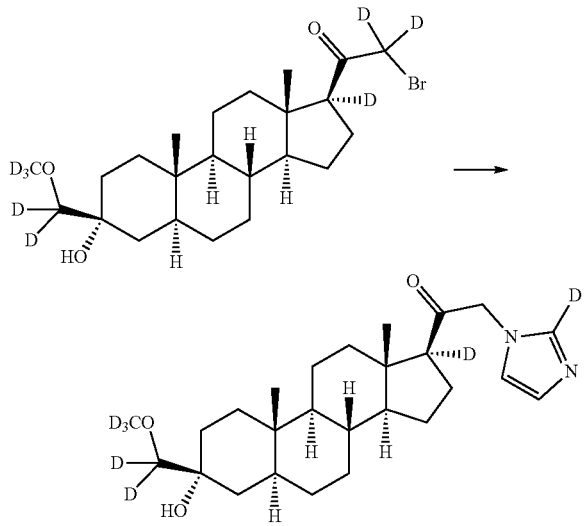

To a solution of imidazole-d1 (0.102 g, 1.48 mmol, 3.0 equiv.) in THF (2.0 mL) is added lithium hydride (0.0128 g, 1.52 mmol, 3.1 equiv.). The solution is stirred at 0° C. for 2 hours under Ar. The compound from Example 7 step 3 (0.221 g, 0.492 mmol, 1.0 equiv.) in THF (3.0 mL) is slowly added to the reaction mixture at 0° C. over a period of 5 min under Ar. After being stirred at 0° C. for 3 hours, the reaction mixture is quenched by D$_2$O (1.50 mL) in ice-bath. The solvent is evaporated, and the residue is purified by flash column chromatography on silica gel to give the corresponding product, then purified again by Semi-Prep HPLC to generate the final product (0.156 g, 0.358 mmol) as white powder in 73% isolated yield. $^1$H NMR (500 MHz, Chloroform-d) δ 7.51-7.30 (m, 1H), 7.13 (d, J=2.5 Hz, 1H), 5.76-5.03 (m, 2H), 2.26-2.14 (m, 1H), 2.10 (d, J=12.2 Hz, 1H), 1.90-1.80 (m, 1H), 1.79-1.73 (m, 1H), 1.73-1.64 (m, 2H), 1.65-1.46 (m, 5H), 1.44-1.15 (m, 10H), 1.07-0.94 (m, 1H), 0.91-0.83 (m, 1H), 0.77 (s, 3H), 0.70 (s, 3H).

Example 12: 1-((3R,5S,8R,9S,10S,13S,14S,17S)-3-hydroxy-3-((methoxy-d3)methyl-d2)-10,13-dimethylhexadecahydro-1H-cyclopenta[a]phenanthren-17-yl-17-d)-2-(1H-imidazol-1-yl-d3)ethan-1-one

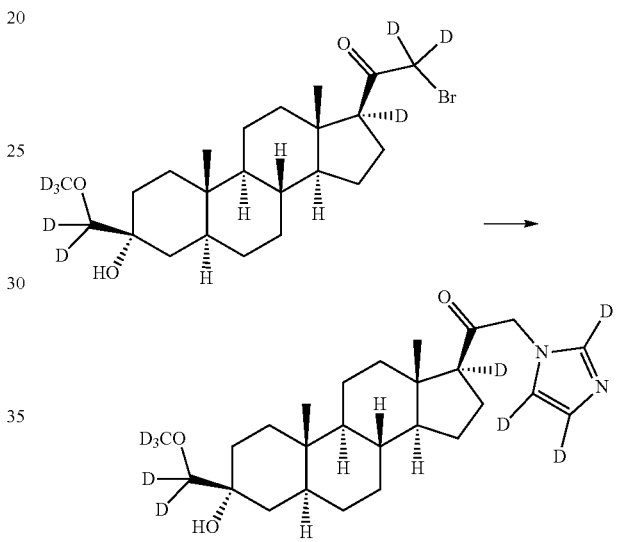

To a solution of imidazole-d4 (0.144 g, 2.00 mmol, 3.0 equiv.) in THF (2.0 mL) is added lithium hydride (0.0174 g, 2.07 mmol, 3.1 equiv.). The solution was stirred at 0° C. for 2 hours under Ar. The compound from Example 7 step 3 (0.300 g, 0.667 mmol, 1.0 equiv.) in THF (3.0 mL) is slowly added to the reaction mixture at 0° C. over a period of 5 min under Ar. After being stirred at 0° C. for 3 hours, the reaction mixture is quenched by D$_2$O (1.50 mL) in ice-bath. The solvent is evaporated, and the residue is purified by flash column chromatography on silica gel to give the corresponding product, then purified again by Semi-Prep HPLC to generate the final product (0.160 g, 0.366 mmol) as white powder in 55% isolated yield. $^1$H NMR (500 MHz, Chloroform-d) δ 5.04-4.56 (m, 2H), 2.30-2.13 (m, 1H), 1.98 (dt, J=11.8, 3.4 Hz, 1H), 1.82-1.66 (m, 4H), 1.63-1.52 (m, 3H), 1.51-1.14 (m, 11H), 1.07-0.93 (m, 1H), 0.93-0.83 (m, 1H), 0.78 (s, 3H), 0.68 (s, 3H).

Example 13: Other Analogs of 3α-Hydroxy-21-(1'-imidazolyl)-3β-methoxymethyl-5α-pregnan-20-one Other deuterated analogs of compounds within the scope of the present disclosure may be made by appropriate means known to those skilled in the art by using deuterated reagents in place of normal reagents, following the prior art reference procedures noted supra. For example:

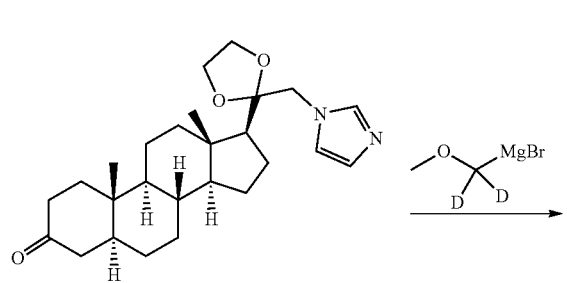
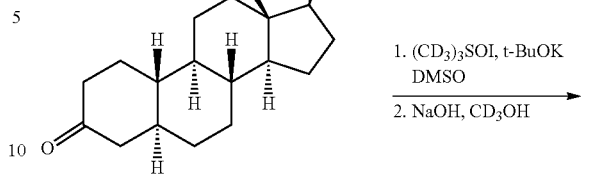
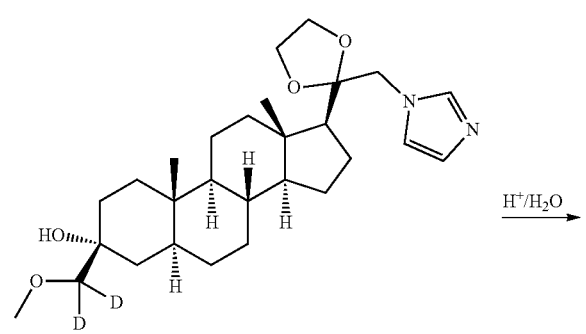
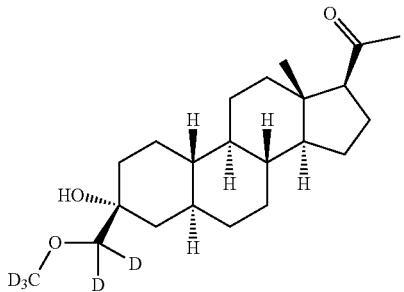
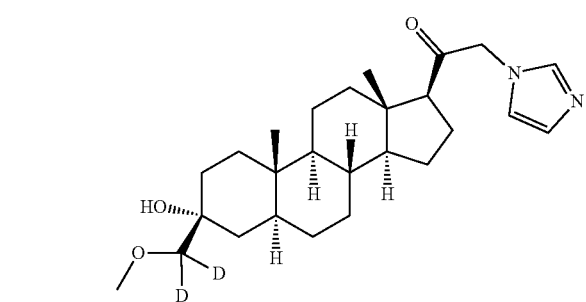
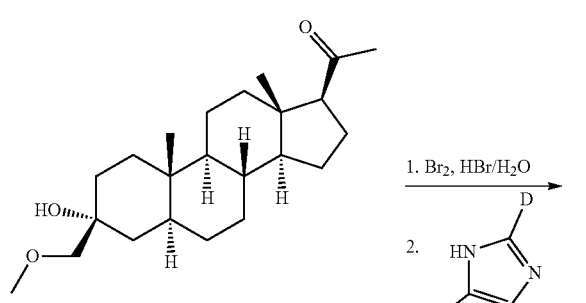

Example 14: Pharmacologic Activity of 3α-Hydroxy-21-(1'-imidazolyl)-3β-methoxymethyl-5α-pregnan-20-one In vitro potency [ability to inhibit the binding of [$^{35}$S]-tert-butylbicyclophosphorothionate (TBPS)], rotorod $TD_{50}$'s (dose at which half of animals tested fail to stay on a rotating rod for 1 minute) and the length of time before animals tested are able to pass rotorod test (duration of action) of 3α-Hydroxy-21-(1'-imidazolyl)-3β-methoxymethyl-5α-pregnan-20-one is determined. These methods for measuring in vitro and in vivo activity of compounds of the invention are fully described in U.S. Pat. No. 5,232,917, incorporated herein by reference in its entirety. The TBPS assay gives the in vitro potency of compounds whereas the rotorod assay estimates the sedative/hypnotic activity of compounds. Since the duration of action of a compound is dependent on the dose and will be prolonged at higher doses, the duration of action is measured at the lowest dose at which all of the animals failed the rotorod test. $IC_{50}$ is the dose of steroid inhibiting 50% of specific binding of [$^{35}$S]-tert-butylbicyclophosphorothionate (TBPS). Rotorod $TD_{50}$ is the does at which half of animals fail the rotorod test in rat. Duration of action, measured at the lowest dose where all animals failed the rotorod test, is the time required for all animals tested to once again pass the rotorod test.

The results show that the Compound of Formula A (Example 1), 3α-Hydroxy-21-(1'-imidazolyl)-3β-methoxymethyl-5α-pregnan-20-one, has a TBPS $IC_{50}$ of 138 nM, a rotorod $TD_{50}$ (po) of 28 mg/kg, and a duration of action of 140 minutes.

Example 15: In Vivo Mouse Pharmacokinetics of Deuterated Compounds

In a first study, the compounds of Examples 2 to 6 are compared to the Compound of Formula A (Example 1) using standard procedures in mice. In each test, two compounds are co-dosed in a single animal and the relative pharmacokinetics in plasma and brain is determined. Each test compound is dissolved in polyethylene glycol 400 vehicle, and administered orally at a dose of 10 mg/kg. After single dose oral administration of the test compounds together, plasma

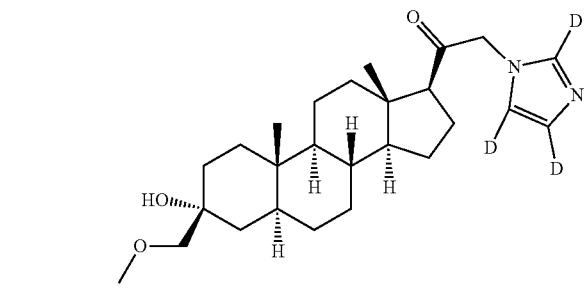

and brain levels are measured at 0.25, 0.5, 1, 2, 4, and 6 hours post-dosing. The mean values for maximum concentration, time to maximum concentration, and Area Under the Curve (AUC) for both compounds are determined. The results are summarized in the tables below for various paired co-dosing experiments:

|  | Plasma (ng/ml) | | Brain (ng/g) | |
| --- | --- | --- | --- | --- |
| Time (hr) | Ex. 1 | Ex. 3 | Ex. 1 | Ex. 3 |
| 0.25 | 2271 | 2173 | 2276 | 2195 |
| 0.5 | 1816 | 1571 | 2234 | 1997 |
| 1 | 2577 | 2424 | 2877 | 2620 |
| 2 | 2098 | 2016 | 2525 | 2374 |
| 4 | 1836 | 1808 | 2365 | 2197 |
| 6 | 1747 | 1721 | 2090 | 1980 |
| Tmax (hr) | 1 | 1 | 1 | 1 |
| Cmax (ng/mL) | 2577 | 2424 | 2877 | 2620 |
| AUC (ng · hr/mL) | 11748 | 11311 | 14172 | 13198 |
| B/P AUC Ratio |  |  | 1.2 | 1.2 |

|  | Plasma (ng/ml) | | Brain (ng/g) | |
| --- | --- | --- | --- | --- |
| Time (hr) | Ex. 2 | Ex. 4 | Ex. 2 | Ex. 4 |
| 0.25 | 1182 | 896 | 1845 | 1708 |
| 0.5 | 1739 | 1486 | 5594 | 5069 |
| 1 | 2547 | 2523 | 7605 | 6531 |
| 2 | 2118 | 1954 | 6344 | 5483 |
| 4 | 1761 | 1596 | 4892 | 4199 |
| 6 | 774 | 423 | 1412 | 1184 |
| Tmax (hr) | 1 | 1 | 1 | 1 |
| Cmax (ng/ml) | 2547 | 2523 | 7605 | 6531 |
| AUC (ng · hr/mL) | 10331 | 9220 | 28975 | 25033 |
| B/P AUC Ratio |  |  | 2.8 | 2.7 |

|  | Plasma (ng/ml) | | Brain (ng/g) | |
| --- | --- | --- | --- | --- |
| Time (hr) | Ex. 5 | Ex. 6 | Ex. 5 | Ex. 6 |
| 0.25 | 1490 | 1406 | 3448 | 3303 |
| 0.5 | 1962 | 1846 | 5541 | 5353 |
| 1 | 2296 | 2118 | 5696 | 5297 |
| 2 | 1771 | 1653 | 5098 | 4884 |
| 4 | 1342 | 1221 | 3183 | 3055 |
| 6 | 725 | 642 | 2236 | 2108 |
| Tmax (hr) | 1 | 1 | 1 | 1 |
| Cmax (ng/ml) | 2296 | 2118 | 5696 | 5353 |
| AUC (ng · hr/mL) | 8896 | 8196 | 23461 | 22350 |
| B/P AUC Ratio |  |  | 2.6 | 2.7 |

These results unexpectedly show that each of the deuterated compounds of Example 2, 4 and 6 provide a much higher brain exposure of drug compared to the non-deuterated compound of Example 1, and thus also, a much higher brain/plasma AUC ratio. In contrast, the deuterated compound of Example 3 provides similar plasma and brain AUC values and B/P ratio as the compound of Example 1. These data suggest that deuteration on or near the imidazole ring favorably affects partition of the compound between the brain and plasma and consequently, leads to higher central nervous system exposure to the drug. This is particularly important as these compounds are neuroactive steroids with intended binding to central nervous system GABA receptors.

Example 16: In Vitro Human Hepatocyte Pharmacokinetics of Deuterated Compounds

The compounds of Examples 1, 2, 5 and 6 are compared in a standard in vitro human hepatocyte stability assay run in duplicate. Compounds are provided as 1 M solutions in DMSO, and concentration of test compound is determined at 0.5, 1.0 and 4.0 hours after addition of the test compound. Results are shown below as a percentage of initial concentration.

| Time (Hr) | Cmpd. Ex. 1 | Cmpd. Ex. 2 | Cmpd Ex. 5 | Cmpd. Ex. 6 |
| --- | --- | --- | --- | --- |
| 0 | 100% | 100% | 100% | 100% |
| 0.5 | 94% | 105% | 83% | 83% |
| 1.0 | 90% | 107% | 80% | 69% |
| 4.0 | 78% | 92% | 52% | 45% |

These results suggest that increasing deuteration of the imidazole may increase metabolic stability of these compounds in hepatocytes (compare Ex. 1 to Ex. 2), while deuteration on the methoxy group or the carbons adjacent to the carbonyl group provides unclear effects.

What is claimed:

1. A compound of a Formula I:

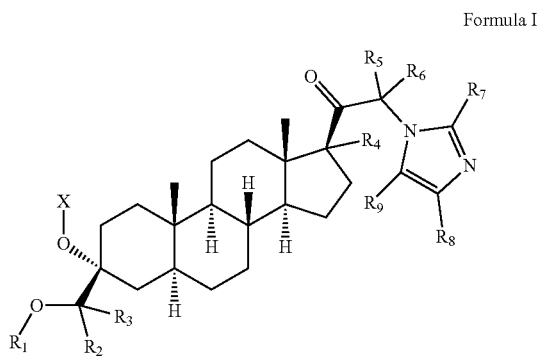

Formula I wherein:
X is selected from H, —(C=O)—$R_a$, —CH$_2$—(C=O)—O—$R_a$, and —CH$_2$—(C=O)—N($R_a$)($R_b$);
$R^1$ is selected from CH$_3$, CDH$_2$, CD$_2$H and CD$_3$;
each of $R^2$ to $R^9$ is independently selected from H and D;
$R_a$ and $R_b$ are independently selected from H, C$_{1-20}$alkyl, and C$_{1-4}$alkyl-aryl;
in free or pharmaceutically acceptable salt form,
provided that if $R^1$ is CH$_3$ and $R^2$ to $R^9$ are all H, then X is selected from —(C=O)—$R_a$, —CH$_2$—(C=O)—O—$R_a$, and —CH$_2$—(C=O)—N($R_a$)($R_b$).

2. A compound according to claim 1, wherein X is H.

3. A compound according to claim 1, wherein X is selected from —(C=O)—$R_a$, —CH$_2$—(C=O)—O—$R_a$, and —CH$_2$—(C=O)—N($R_a$)($R_b$).

4. A compound according to claim 1, wherein X is —(C=O)—$R_a$.

5. A compound according to claim 1, wherein X is —CH$_2$—(C=O)—O—$R_a$.

6. A compound according to claim 1, wherein X is CH$_2$—(C=O)—N($R_a$)($R_b$).

7. A compound according to claim 1, wherein X is CH$_2$—(C=O)—N($R_a$)($R_b$) and $R_b$ is H.

8. A compound according to claim 1, wherein $R^1$ is CH$_3$.

9. A compound according to claim 1, wherein $R^1$ is $CD_3$.

10. A compound according to claim 1, wherein any one or two or three or four of $R^2$ to $R^9$ is D.

11. A compound according to claim 1, wherein $R^2$ and $R^3$ are D.

12. A compound according to claim 1, wherein $R^5$ to $R^6$ are D.

13. A compound according to claim 1, wherein any one, two or three of $R^7$ to $R^9$ are D.

14. A compound according to claim 1, wherein the compound is selected from the group consisting of:

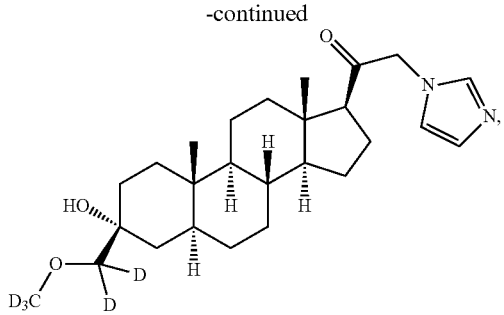

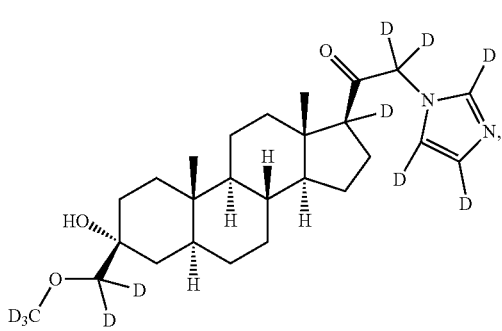

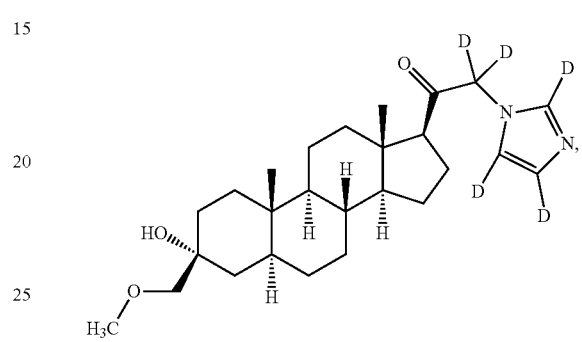

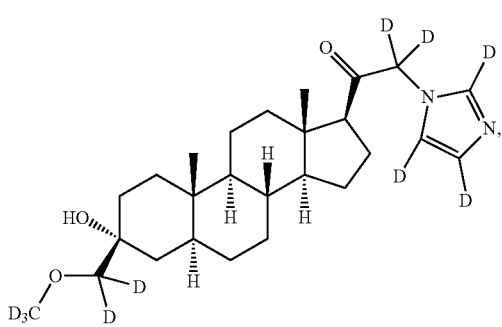

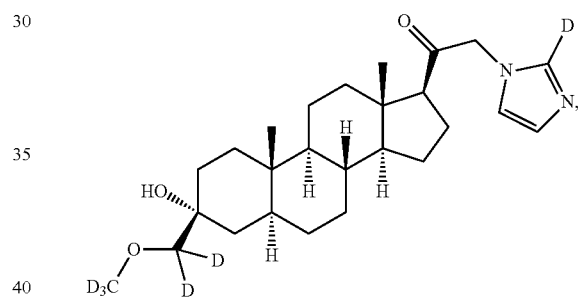

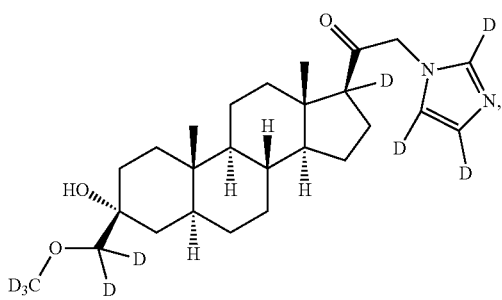

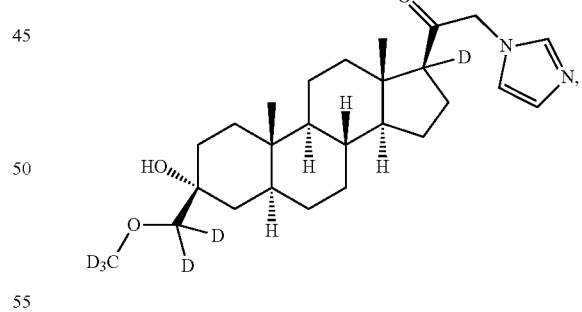

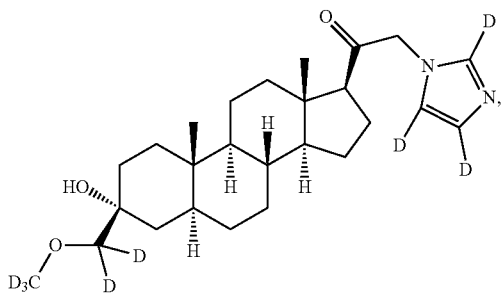

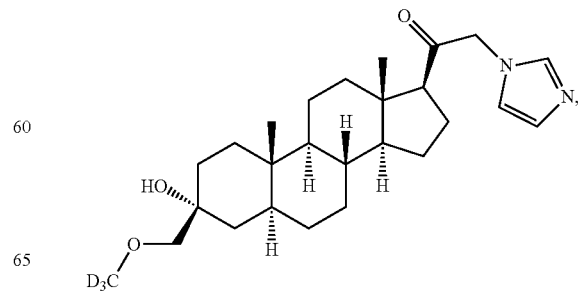

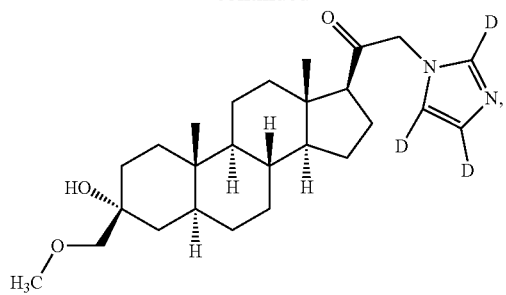
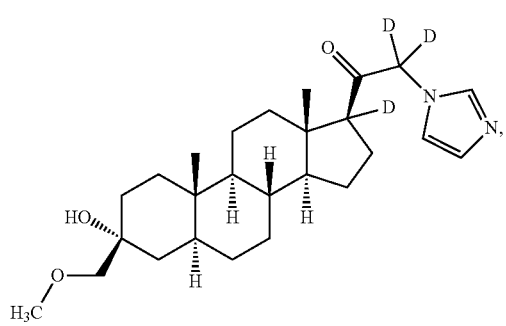
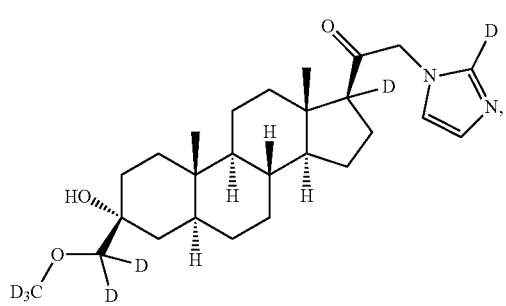
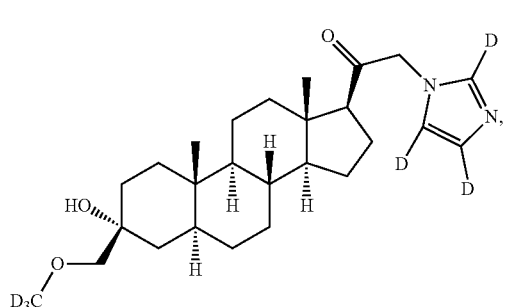
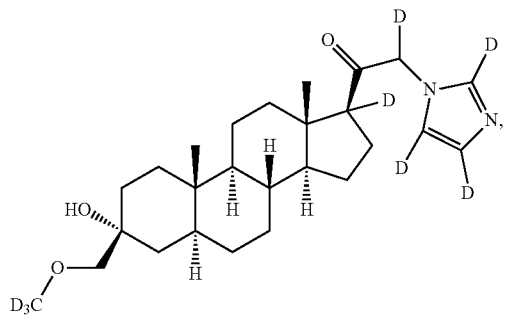

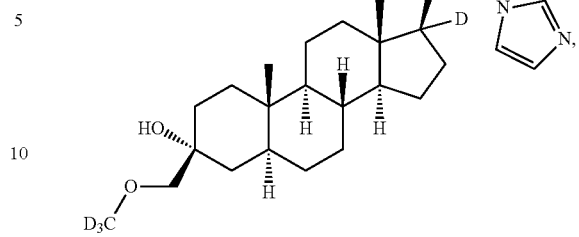
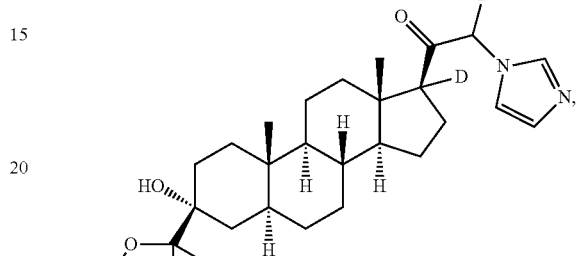
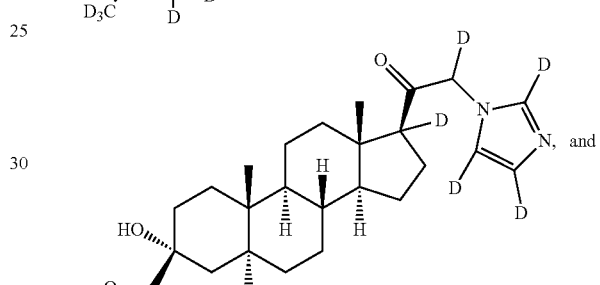

15. A compound according to claim 1, in the form of a pharmaceutically acceptable salt.

16. A compound according to claim 1, having greater than 90% incorporation of deuterium at one or more of the indicated positions of the structure.

17. A pharmaceutical composition comprising a compound according to claim 1, in free or pharmaceutically acceptable salt form, in admixture with a pharmaceutically acceptable diluent or carrier.

18. The pharmaceutical composition of claim 17, wherein the composition is an oral dosage form.

19. The pharmaceutical composition of claim 17, wherein the composition is formulated as a long acting injectable.

20. A method for the treatment of a central nervous system disorder amenable to amelioration using a $GABA_A$ receptor modulator, comprising administering to a patient in need thereof a compound according to claim 1, in free or pharmaceutically acceptable salt form.

21. The method according to claim 20, wherein said disorder is selected from a group consisting of sleep disorders, circadian rhythm disorders, phase shift disorders, anxiety, post-traumatic stress disorder, depression, compulsive disorders, schizophrenia, schizoaffective disorder, attention disorders, convulsive disorders, disorders of aggression, agitation disorders, disorders of memory and/or cognition, movement disorders, autism and autism spectrum disorders, pain disorders, personality disorders, vascular disorders, eating disorders, traumatic brain injury, substance abuse disorders, substance use disorders, substance withdrawal syndromes, Rett Syndrome, Fragile X Syndrome, Angelman Syndrome, and tinnitus, and neurodegenerative diseases and disorders requiring sedation or anesthesia for effective treatment.

22. A method of inducing sedation or anesthesia in a patient in need thereof, wherein the method comprises the administration of a compound according to claim 1, in free or pharmaceutically acceptable salt form, to a patient in need thereof.

23. A compound according to claim 1, wherein $R^7$ to $R^9$ are each D.

24. A compound according to claim 1, wherein $R^7$ is D.

25. A compound according to claim 1, wherein X is H, $R^1$ is $CH_3$, and $R^2$ and $R^3$ are H.

26. A compound according to claim 25, wherein $R^7$ to $R^9$ are each D.

27. A compound according to claim 25, wherein $R^7$ is D.

28. The method according to claim 21, wherein said disorder is selected from a group consisting of insomnia, jet lag, general anxiety, social anxiety, panic disorders, refractory depression, major depressive disorder, bipolar depression, postpartum depression, seasonal affective disorder, dysthymia, treatment-resistant depression, suicidal ideation, suicidal behavior, pre-menstrual dysphoric disorder, obsessive-compulsive disorder, attention-deficit disorder, attention deficit-hyperactivity disorder, seizure disorders, epilepsy, status epilepticus, acute or chronic aggression, acute or chronic agitation, Alzheimer's disease, senility, Lewy body dementia, vascular dementia, Parkinson's disease, Huntington's disease, tremors, Asperger's syndrome, neuropathic pain, acute pain, chronic pain, anti-social personality disorder, depressive personality disorder, stroke, ischemia, vascular malformations, bulimia, anorexia, binge-eating disorder, cachexia, amyotrophic lateral sclerosis, coma, dyskinesias, and dystonias.

* * * * *